US010711279B2

(12) United States Patent
Ernst et al.

(10) Patent No.: US 10,711,279 B2
(45) Date of Patent: Jul. 14, 2020

(54) PROMOTER SEQUENCES

(75) Inventors: Wolfgang Ernst, Pottendorf (AT); Jens Pontiller, Vienna (AT); Friedemann Hesse, Warthausen (DE); Haruthai Thaisuchat, Kanchanaburi (TH)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 13/518,152

(22) PCT Filed: Dec. 22, 2010

(86) PCT No.: PCT/EP2010/070537
§ 371 (c)(1),
(2), (4) Date: Jun. 21, 2012

(87) PCT Pub. No.: WO2011/076870
PCT Pub. Date: Jun. 30, 2011

(65) Prior Publication Data
US 2012/0258493 A1 Oct. 11, 2012

(30) Foreign Application Priority Data
Dec. 22, 2009 (EP) .................................... 09180432

(51) Int. Cl.
*C12N 15/85* (2006.01)
(52) U.S. Cl.
CPC ........ *C12N 15/85* (2013.01); *C12N 2830/002* (2013.01)
(58) Field of Classification Search
None
See application file for complete search history.

(56) References Cited

U.S. PATENT DOCUMENTS

2008/0039413 A1* 2/2008 Morris ................. C12Q 1/6886
514/44 R

FOREIGN PATENT DOCUMENTS

WO      WO-9919481 A2 *   4/1999   ............. C07K 14/47

OTHER PUBLICATIONS

Thaisuchat et al in "Identification of a novel temperature sensitive promoter in cho cells" (BMC Biotechnology: 2011, vol. 11:51; pp. 1-12).*
Horvath et al in "Divergent evolution of human p53 binding sites: cell cycle versus apoptosis" (Pl o S Genetics Jul. 2007 vol. 3, No. 7: p. 1284: 15 pages).*
Score result 6 to SEQ ID No. 2 for Morris & Malandro US2008/039413 (Feb. 14, 2008) (Year: 2008).*
Score result US2008/0039413 SEQ ID No. 2 (Year: 2008).*
Score result US2008/0039413 SEQ ID No. 1 (Year: 2008).*
Score result 1 and 2 for Munzy et al SEQ ID No. 3 (Year: 2002).*
Score result WO9919481 SEQ ID No. 1 (Year: 1999).*
Database EMBL [Online] Oct. 25, 2001 (Oct. 25, 2001), "Rattus norvegicus clone CH230-3917, Working Draft Sequence, 8 ordered pieces," XP002580110, retrieved from EBI accession No. EMBL:AC097705, Database Accession No. AC097705.
Kumar, Niraj et al., "Differential protein expression following low temperature culture of suspension CHO-K1 cells," MBC Biotechnolog, vol. 8, Apr. 2008, XP002580111.
Al-Fageeh, Mohamed B. et al., "Control and regulation of the cellular responses to cold shock: the responses in yeast and mammalian systems," The Biochemical Journal, Jul. 15, 2006, vol. 397, No. 2, pp. 247-259, XP002580112.
Kaufmann, H. et al., "Influence of low temperature on productivity, proteome and protein phosphorylation of CHO cells," Biotechnology and Bioengineering, Jun. 5, 1999, vol. 63, No. 5, pp. 573-582, XP002580113.
Zervos, E. E. et al., "Differential gene expression in patients genetically predisposed to pancreatic cancer," Journal of Surgical Research, Academic Press Inc., San Diego, CA, US, vol. 135, No. 2, Oct. 1, 2006, pp. 317-322, XP024952589.
Database EMBL [Online], "CCUA4141.b1 CCUA Peromyscus polionotus subgrisieus PO:Br,Ts Peromyscus polionotus subgriseus cDNA clone CCUA4141 5', mRNA sequence," Database accession No. GH462428, Jan. 10, 2009.
Database MBL [Online], "AMGNNUC:NRDG1-00083-B6-Anrdg1 (10855) Rattus norvegicus cDNA clone nrdg1-00083-b6 5' mRNA sequence," Database accession No. C8609823, Apr. 5, 2003.
Database Geneseq [Online] Jul. 24, 1999, "Rat U3 gene trap derived nucleic acid L25-10/-rE.", retrieved from EBI Accession No. GSN:AAX57481.
European Examination Report, dated Jan. 23, 2015, for European Application No. 10 796 393.6.
Thaisuchat et al., "Identification of a novel temperature sensitive promoter in cho cells", BMC Biotechnology, vol. 11, No. 1, 2011, pp. 51-63, XP21099635A.
European Examination Report issued in European Patent Application No. 10 796 393.6 dated Sep. 14, 2015.
Lee et al., "Uncoupling gene activity from chromatin structure: Promoter mutations can inactivate transcription of the yeast HSP82 gene without eliminating nucleosome-free regions", Proc. Natl. Acad. Sci. USA, vol. 89, No. 19 (1992) pp. 9166-9170.
Rohan et al., "A Comprehensive Collection of Point Mutations in the Internal Promoter of the Adenoviral VA1 Gene", The Journal of Biological Chemistry, vol. 262, No. 18 (1987) pp. 8500-8507.

* cited by examiner

*Primary Examiner* — Catherine S Hibbert
(74) *Attorney, Agent, or Firm* — Birch, Stewart, Kolasch & Birch, LLP

(57) ABSTRACT

The present invention relates to new promoter sequences and uses thereof, in particular expression cassettes, vectors, and methods of expressing genes using the new promoters.

21 Claims, 9 Drawing Sheets

Figure 1:
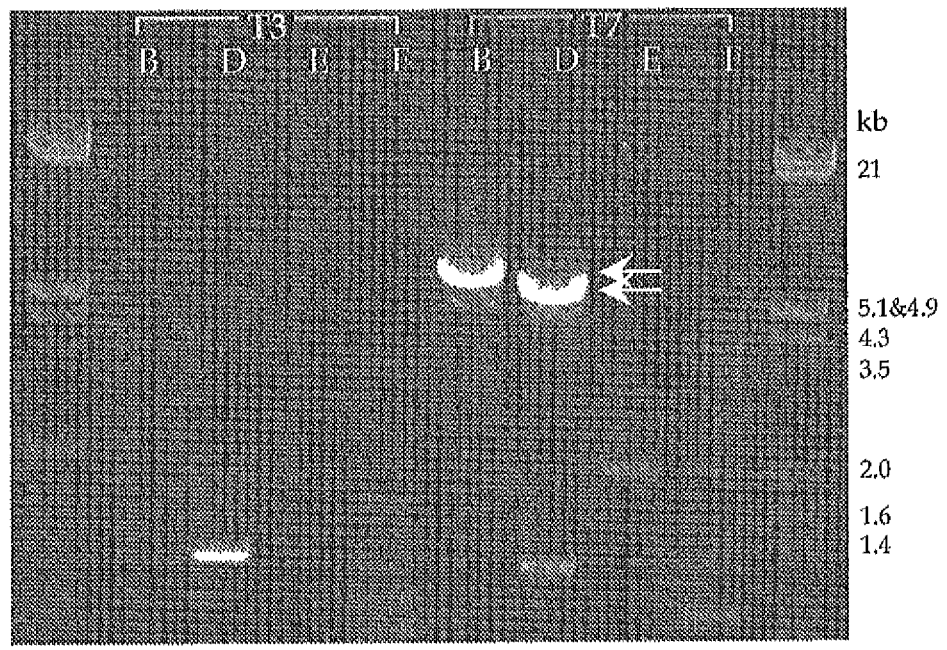

Specification includes a Sequence Listing.

Fig. 2 A:
SEQ ID NO 1
GCATGCTGGCTGGGCTGGGCTCCATTGTGTGCACATTAATTTGTAAGCTGCTCTAAAGATGA
ACTTCCAGGCAGTGAGCTGGAAGAAGCGAGTTAGACAGAAATTTATTGTTGGTGGGGATGG
TGTCTGAAATCCTTTAGACTGTGTCCCTCCCCTTTTTTGAGACAGGGTTTTATATAGCCCA
GGTTGGCTCAGAATTCTGCCTCGTGGGATCAACCTACTGAGCTATATCCCCAAGTCTTAAAC
TAGTGAGGTCAAACCACCCTATCAGAGGGGTTGCCTAAGATCATCGGAAAACACAAGTATTT
ACACTGAGATTCATAACAGTAGCAAAATTACGGTGTGAAGCAGCAGTGAAAATAATTTTATG
ATTGGGGACACCACAACATGAGAATCTGTGTCCAAGGGTCATAGAATTAGGAAGGTTGAGA
ACTATTAGCCAATCTAGTAGACCACTAGGGCTTCCCCTCCTTCCCTGGAGCTGACCTTGCC
ACCAGAGGGCGACAGCATCAGTGAGGTTCCCACTCCCCCTCACATTGATGCTGACTTTAGGG
ACACATTGTGCTCTGTCTGGCAGATGGCCCAGCACACATGCCGGAGTCACGAGTCACGTGCC
ATAAGGGCAAACTGAAGTATGGAAATTAGGGAAAACTCGATGTCTCTGGTTTGTGCTGGTCT
CCCAGACCAGGGTCACTAGGCTCCCTCATGCCACTCCCAATCCGGGACAGTCCTGGCAGCAG
AGGCGTGGAAAACTGAGGGGGTTGTTGGGGTGTGTTTTGCTAGCCTCAGGCGCCGGGTGGGG
CTCGGGGCGGGCCGGCACTCCTTGGGCGGGCCTCCCGGATGCTAGCCGCTATAAGGCCAGCC
GGACTGCGACACAGTCCATCCCCTCGACCACTCCTTTGGCTCTTCGCTGTCTACCTGCCTAC
GGTGCGGTGAGCTCTTGCTGGGGCAGTTCTAGGTCCCTCTAAGGTCGGCTCCTGGGCTGGGG
GGTCAAGCCACTTCCTGCCACATCCAGCCCCTACGGGTTCCGCGGGTGGTCTACACTGGGGT
CTAAATCTGCCGAGCACGGGGTGGTGGGGGTGGGGGTGGGGTGGGGTGGGCAGGTAAGAGG
GGGAGGTAGGGAGAGCCAAGGTTCAGCTTGGTTGTGCCAGGCAAGCCCGGAGGCTAAGGCAT
CCTTATAGGGCGGCTCCCCGAGTCTGCTTTTCTGGGGTGCAGGAGGGTTCGCCCTGGGTGTG
TCATTGTCGTCGCAGTGTGTGGTCCTGTCAGGAAGTGCCCTGGAGCAGCCTCCATCTCTTCC
TCTGCTCAGTCATATTCCCCAGCTCTCTTGGAATCCCTGGAGATCAGTGTTCAGACACCCCA
AAGCCGCTTCCGTTCTTACATCCCTGACCCTAGTTGCCCTGGGCTGCCTGCACCTGTGTTGG
CTAAGGCTAGCTGGTTCAGACAGGCAGCACTGACTAGCCCCTCTCTGTCAAACAGCTTCTTC
TAGCCCAGTGGTCAATT

Fig. 2 B:
SEQ ID NO 2
TCAAAACTTTTCACTTGAGATGAGTAACTGAGAATGCTCGCTGGGCTTGGCTCTACTATGTGCACATTCATGCAT
AAGCTGCTCTAAGGATGAAAATCCAGGCAGTGAGTGGGAGGAGGCGAGTGATGTTGCTAGAAATTTATGGTTGGT
GGGGGATGCTGTTTAAAATCTTTTAGACTGTGTTCTTTCCCCATGCCCCCTTTGATACAAGGCTCAAAATTCTAC
CTTTTGGGATCAACGTCTTTAGCTATATATCAAGATTTAGACCAGTGGTTCTCAACCTGTGGGTTGAGACCCCTT
TCACAGGAATTGCCTAAGACCATCTGAAAACACAGATATACACATTAAGATTCATAACAGTAGCAAAATTATAGC
TATGAAGTAGAAACGAGAATAACTTTATGATTGGGGGACCACCACAACTTGAAGAACAGTATTAAAGGGCCGCAG
CATTAGTCAGGTTGAGTGAGAACCATTTCTTAGAGGATGTGGTAGACAGACTGCTTCCCCTCCCTCACTTGGGGA
CCTTGCCACTAGAGGGCAACAGCATCAGTGTGGTTCCCAGTCCCCCTCACACTGATGCTAACTTTAAGGACACTG
CTCTCGGGCTGGCAGAAGGTTCAGCACACAAGCCAGAGTTTCGAGTCACGTGCCAGAAGGGAAAACTAAACACGG
AATTAGAGAAAACTTGATGCCTCTGGCTTGCACTGGTCTCCTTTGGGCCCGTTAGGGCCCGCTAAACTCCCTCAT
TCCGCTCCTAATCCTGGACAGTCCAGGCAACAGGGGCGTGGAAAGTTGAGGGGGCTGGGATGTTCGTTTGCCTTG
CCTCAGGCGCTGGGTGGGGTCGGGGCGTGCCAGCACTCCCTGGGCGGACCTCACGGATGCTGGCCACTATAAGGC
CGGCCAGACTGCGACACATTCCATCCCCTCGACCACTCCTTTTGGCGCTTCGCTGTCGACCGTGCGGTGAGCTCTC
GCTGGGGGGTCCCTCTAGGGTCTTTCTGCTCCTGGGCAAGGGGTTAAGCCACTTCCTTCCCCCGTCAGCCTCTGC
AGGCTCAGTGGGTGGAATGCATTGGGATCCAAGTTTTCGGAGCCCAGGGAGGCAGGGAGAGCCATGATTAGGTGG
GTTGTATCAGGCAAACCCAGAGGCTAATGCATCCCTATGGGGCGGCAACCTGAGTCTGCTCTTCTGGGGTGCAGG
AGGGTTTGCCCTGGGTGTGTCATCGTCCCAGTGTGTGGCTATGTCAGGAGGTGCCCAGGGGCACTCTCCATTCTC
TTCCTTGCTCAGTCATATGCCCTAGTTCTCTTGGAAGCCCTGGAGGACAGTGCTCACAGATCCCAAAGCCCCTTC
CATTCTTATATCCCTCACCTAAGTTGCCCCGGCTGCCACCTGTGTTGGCTTGAGACTGACTGCCTCAGGCAGGGG
GGTGGTGAGAGAACTCTCTGCTATCAGCAGCACTGACTAGCCCCTCTGTCAAACAGCTTCTTCTAGCCCAGTGAT
CAGTC

Fig. 2 C:
SEQ ID NO 3
TGAAAACTTTTTACTTGAGATGAGTAAGTAACTAACGATGCTTCCTGGGCTTGGCTCCACTGTGTGCACATTAAG
GCATAAGCTGCTCTGAGGATGAAATTCCAGGCAGTGAGTGGGAGGAGGCAAGTGATGTTGTTAGAAATTTATGGT
TGGTGGGGGATGCTGTTTAAAATCTTTTAGACTGTGTTCCCCTTCTGTCTCCTTTTGAGACATGGGTCTTATAT
AGGTTGGCTCAAAATTCTACCTCTTGGGATCAGCCTATCTCATCAAGATTTAGCCCAGTGGTGCTCAACCTGTGG
AGACCCCTTTCACAGGAATTGCCTGAGACCATCTGAAAACACAGTATTTATGTCACGATTCATAACAGTAGCAAA
AATATAGTTATGAAGCAGCAACGAAAATCACTTTATGGTTGGAGCGTCACCACAACATGAAGAATGTATTAATCC
GCAGTATTAGAGAGGTCGAGAACCACTATCTTAGAGGATGCGGTAGACTGACTGCTTCCCCTCTCGCTTGGAGTT
GACCTTGCCACTAGAGGGCAACAGCATCAGTATTGTTCCCAGTCCCCCTCACACTGATTCGAACTTTAAGGACAC
TGATCTCTGGCTGGTAGAGGGTTCAGCACACATACCAGAGTTACGAGTCACGTGCCAGAAGGGCAAACTGAACAC
GGAATTAGAGGGAACTCGATGTCTCCGGCTTGCACTGGTCTTCTCTTGCACTAGAATCCTTCATCCTGCTCCCAG
TCCGGGACGTCCAGGCAACAAGGGCGTGGAAAGTGAGGGGGCTGGGAGGTGTGTTTGCCTTGCCTCAGGCGCTGG
GTGGGGTTGGGGCGTGCCAGCACTCCCTGGGCGGGCCTCACCGATGCTGGCCACTATAAGGCCAGCCAGACTGCG
ACACAGTCCATCCCCTCGACCACTCTTTTGGCGCTTCATTGTCGACGTGTGGTGAGCTCTCACTGGGGCGTCCCT
CTAAGATCTGTCCACTCCTGGTCTAGGGGTTAAGCCTTTCCTGCCCTAGTCAGCCTCTGCGGGCTCCATGGGTGG
AATGCACTGGGATCCAAGTTTTCGGAGCCCAGGGAAGCAGGGAGAGCCATGGTCTGCTGGGCTGTACCAGACAAA
CCCCGAGGCTAAGGCATCCCCATGGGCGGCAACCTGAATCTGCTTTTCTGGGGTGCAGGAGGGTTTGCCCTGGGT
GTGTCATCCTCGTCCCAGTGTGTGGCCCTGTCAGGAGGTTTCCAGGGGCAGCCTCCATTCTCTTCCTTGCTCAGT
CATATGCTCCAGTTCTCTTGGAAGCCCTGGAGGACAGTGTTCACAGACCCCAAAGCCCTTCCATTCTTAGACTC
CTCACCTCAGTGGCCCTGGCTGCTACCTGTGTTGGCTTGAGGCTAGCTGCTTCAGGCAGGTAGTCTCCTGGCTCA
GGGGATGGTGAGAGGACTCTCTGCTACCAGTAGCACTGAATAGCCCCTCTGTCAAACAGCTTCTAGCCCAGTGGT
CAGTC

Fig. 4: A:

```
                                  NF-κB
mouse    CCTCATTCCGCTCCTAATCCTGGACAGTCCAGGCAACAGGGGCGTGGAAAGTTGAGGGGG   -702
rat      CTTCATCCTGCTCCCAGTCCGGGAC-GTCCAGGCAACAAGGGCGTGGAAAGT-GAGGGGG   -715
CHO      CCTCATGCCACTCCCAATCCGGGACAGTCCTGGCAGCAGAGGCGTGGAAAACTGAGGGGG   -741
         * ****  * ****   *** **** ****  **** **  ********   ****** *
                                                            Sp1
mouse    CTGG-GATGTTCGTTTGCCTTGCCTCAGGCGCTGGGTGGGG-TCGGGCGTGCCAGCACT   -644
rat      CTGG-GAGGTGTGTTTGCCTTGCCTCAGGCGCTGGGTGGGG-TTGGGCGTGCCAGCACT   -657
CHO      TTGTTGGGGTGTGTTTGCTAGCCTCAGGCGCCGGGTGGGGCTCGGGCGGGCCGGCACT   -681
         **   *  ** ****  ** **********  ********  * ***** *** *****
            Sp1                       TATA
mouse    CCCTGGGCGGACCTCACGGATGCTGGCCACTATAAGGCCGGCCAGACTGCGACACATTCC   -584
rat      CCCTGGGCGGGCCTCACCGATGCTGGCCACTATAAGGCCAGCCAGACTGCGACACAGTCC   -597
CHO      CCTTGGGCGGGCCTCCCGGATGCTAGCCGCTATAAGGCCAGCCGGACTGCGACACAGTCC   -621
         **  ******* **** * ****** *** **  ****** *** ***  ********* ***
```

Fig. 4: B:

```
mm    TCAAAACTTTTCACTTGAGATGAGT----AACTGAGAATGCTCGCTGGGCTTGGCTCTAC
rn    TGAAAACTTTTTACTTGAGATGAGTAAGTAACTAACGATGCTTCCTGGGCTTGGCTCCAC
cg    ------------------------------GCATGCTGGCTGGGCTGGGCTCCAT
                                     ***  *** *** * mm    TATGTGCACATTCATGCATAAGCTGCTCTAAGGATGAAAATCCAGGCAGTGAGTGGGAGG
rn    TGTGTGCACATTAAGGCATAAGCTGCTCTGAGGATGAAATTCCAGGCAGTGAGTGGGAGG
cg    TGTGTGCACATTAATTTGTAAGCTGCTCTAAAGATGAACTTCCAGGCAGTGAGCTGGAAG
      * **********  *       *********** * ****  ****** * * mm    AGGCGAGTGATGTTGCTAGAAATTTATGGTTGGTGGGGGATGCTGTTTAAAATCTTTTAG
rn    AGGCAAGTGATGTTGTTAGAAATTTATGGTTGGTGGGGGATGCTGTTTAAAATCTTTTAG
cg    AAGCGAGT----TAGACAGAAATTTATTGTTGGTGGGGGATGGTGTCTGAAATCCTTTAG
      *  *     *  * ******* ********** *  *  *** *** mm    ACTGTGTTCTTTCCCCATGCCCCCTTTGATACAAGG--------------------CTCA
rn    ACTGTGTTCCCCTTCTGTCTCCCTTTTGAGACATGGGTCTT----ATATAGGTTGGCTCA
cg    ACTGTGTCCCTCCCC-----CTTTTTTGAGACAGGGTTTTATATAGCCCAGGTTGGCTCA
      *******  *    *        *   *** *                 ** mm    AAATTCTACCTTTTGGGATCAACGTCTTTAGCTATA-TATCAAGATTTAGACCAGTGGTT
rn    AAATTCTACCTCTTGGGATCAGCCTATCT--------CATCAAGATTTAGCCCAGTGGTG
cg    GAATTCTGCCTCGTGGGATCAACCTACTGAGCTATATCCCCAAGTCTTAAACTAGTGAGG
       **** * ********  *        *    **    *  *  **** mm    CTCAACCTGTGGGTTGAGACCCCTTTCACAGGAATTGCCTAAGACCATCTGAAAACACAG
rn    CTCAACCTGTGG----AGACCCCTTTCACAGGAATTGCCTGAGACCATCTGAAAACACAG
cg    TCAAACC-------------ACCCTATCAGAGGGGTTGCCTAAGATCATCGGAAAACACAA
       * **               * * * * ******  *****  * mm    ATATACACATTAAGATTCATAACAGTAGCAAAATTATAGCTATGAAGTAGAAACGAGAAT
rn    -TATTTATGTCACGATTCATAATAGTAGCAAAAATATAGTTATGAAGCAGCAACGAAAAT
cg    GTATTTACACTGAGATTCATAACAGTAGCAAAATTACGG-TGTGAAGCAGCAGTGAAAAT
       ***  *       ****************   *  * ***     *** mm    AACTTTATGATTGGGGGACCACCACAACTTGAAGAACAGTATTAAAGGGCCGCAGCATTA
rn    CACTTTATGGTTGCAGCGTCACCACAACATGAAGAAT-GTATTAAT---CCGCAGTATTA
cg    AATTTTATGATTGGGGGA-CACCACAACATGAGAATCTGTGTCCAAGGGTCATAGAATTA
        * ******  **       ********  ***  ***  * ***       **  ******
```

Fig. 4B (continued)

```
mm      GTCAGGTTGAGTGAGAACCATT-TCTTAGAGGATGTGGTAGAC---AGACTGCTTCCCCT
rn      GAGAGGTCGAG----AACCACTATCTTAGAGCATGCGCTACAC---TGACTGCTTCCCCT
cg      GGAAGGTTGAG----AACTATT-----AGCCAATCTAGTAGACCACTAGGGGCTTCCCCT
        *  ** *    *** * *           ****        ******* mm      CCCTCACTTGGG---GACCTTGCCACTAGAGGGCAACAGCATCAGTGTGGTTCCCAGTCC
rn      C--TCGCTTGGAGTTGACCTTGCCACTAGAGGGCAACAGCATCAGTATTGTTCCCAGTCC
cg      CCTTC-CCTGGAGCTGACCTTGCCACCAGAGGGCGACAGCATCAGTGAGGTTCCCACTCC
        *  ** * *      ****** ** ********  *** * mm      CCCTCACACTGATGCTAACTTTAAGGACAC--TGCTCTCGGGCTGGCAGAAGGTTCAGCA
rn      CCCTCACACTGATTCGAACTTTAAGGACAC--TGATCTCTGGCTGGTAGAGGGTTCAGCA
cg      CCCTCACATTGATGCTGACTTTAGGGACACATTGTGCTCTGTCTGGCAGATGGCCCAGCA
        ****** ** *  **** **      *** * **     *** mm      CACAAGCCAGAGTTTCGAGTCACGTGCCAGAAGGGAAAACTAAA-CACGGAA-TTAGAGA
rn      CACATACCAGAGTTACGAGTCACGTGCCAGAAGGGCAAACTGAA-CACGGAA-TTAGAGG
cg      CACATGCCGGAGTCACGAGTCACGTGCCATAAGGGCAAACTGAAGTATGGAAATTAGGGA
        **   **  ********** * **   * ** ** * mm      AAACTTGATGCCTCTGGCTTGCACTGGTCTCCTTTGGGCCCGTTAGGGCCCGCTAAACTC
rn      GAACTCGATGTCTCCGGCTTGCACTGGTCTTCTCTTG-------------CACTAGAATC
cg      AAACTCGATGTCTCTGGTTTGTGCTGGTCTCCCAGACC-------AGGGTCACTAGGCTC
        **  * *        ***** *           *   * * mm      CCTCATTCCGCTCCTAATCCTGGACAGTCCAGGCAACAGGGGCGTGGAAAGTTGAGGGGG
rn      CTTCATCCTGCTCCCAGTCCGGGAC-GTCCAGGCAACAAGGGCGTGGAAAGT-GAGGGGG
cg      CCTCATGCCACTCCCAATCCGGGACAGTCCTGGCAGCAGAGGCGTGGAAAACTGAGGGGG
        * ****  * * *            ********    ***** mm      CTGG-GATGTTCGTTTGCCTTGCCTCAGGCGCTGGGTGGGG-TCGGGGCGTGCCAGCACT
rn      CTGG-GAGGTGTGTTTGCCTTGCCTCAGGCGCTGGGTGGGG-TTGGGGCGTGCCAGCACT
cg      TTGTTGGGGTGTGTTTTGCTAGCCTCAGGCGCCGGGTGGGGCTCGGGGCGGGCCGGCACT
        **   *       ******** ***** * **** * ***** mm      CCCTGGGCGGACCTCACGGATGCTGGCCACTATAAGGCCGGCCAGACTGCGACACATTCC
rn      CCCTGGGCGGGCCTCACCGATGCTGGCCACTATAAGGCCAGCCAGACTGCGACACAGTCC
cg      CCTTGGGCGGGCCTCCCGGATGCTAGCCGCTATAAGGCCAGCCGGACTGCGACACAGTCC
         **  ** * **** * **********  * ******** * mm      ATCCCCTCGACCACTCCTTTGGCGCTTCGCTGTCGACC--------GTGCGGTGAGCTCT
rn      ATCCCCTCGACCACTCTTTTGGCGCTTCATTGTCGAC---------GTGTGGTGAGCTCT
cg      ATCCCCTCGACCACTCCTTTGGCTCTTCGCTGTCTACCTGCCTACGGTGCGGTGAGCTCT
        ************** **  **  * **  *     * ******** mm      CGCTGGGGG--------GTCCCTCTAGGGTCTTTCTGCTCCTGGGCAAGGGG-TTAAGCC
rn      CACTGGGGC--------GTCCCTCTAAGATCTGTCCACTCCTGGTCTAGGGG-TTAAGCC
cg      TGCTGGGGCAGTTCTAGGTCCCTCTAAGGTCC----GCTCCTGCGCTCGCGGCTCAACCC
         ***                ******* * *  ****** *    * *  *  * ***** mm      ACTTCCTTCCCCCGTCAGCCTCTGCAGGCTCAGTGGGTGGAATGCATTGGGATCCAAGTT
rn      -TTTCCTGCCCTAGTCAGCCTCTGCGGGCTCCATGGGTGGAATGCACTGGGATCCAAGTT
cg      ACTTCCTGCCACATCCAGCCCCTACGGGTTCCGCGGGTGGTCTACACTGGGGTCTAAATC
          ***      ***    ***  *     *   * *   * mm      TTCGGAGCCCAGGG---------------------------------------------AG
rn      TTCGGAGCCCAGGG---------------------------------------------AA
cg      TGCCGAGCACGGGGTGGTGGGGTGGGGGTGGGGTGGGTGGGGAGGTAAGAGGGGAG
         * * **** * ***                                              * mm      GCAGGGAGAGCCATGAT-TAGGTGGGTTGTATCAGGCAAACCCAGAGGCTAATGCATCCC
rn      GCAGGGAGAGCCATGGT-CTGCTGGGCTGTACCAGACAAACCCCGAGGCTAAGGCATCCC
cg      GTAGGGAGAGCCAAGGTTCAGCTTGGTTGTGCCAGGCAAGCCCGGAGGCTAAGGCATCCT
        *  **********   * *  * **  ***   ***  *** *** ******* ******
```

Fig. 4B (continued)

```
mm      TATGGGGCGGCAACCTGAGTCTGCTCTTCTGCGGTGCAGGAGGCTTTGCCCTCGGTGTCT
rn      CATGGG-CGGCAACCTGAATCTGCTTTTCTGGGGTGCAGGAGGGTTTGCCCTGGGTGTGT
cg      TATAGGGCGGCTCCCCGAGTCTGCTTTTCTGGGGTGCAGGAGGGTTCGCCCTGGGTGTGT
          **    **  *************** *********** mm      CAT---CGTCCCAGTGTGTGGCTATGTCAGGAGGTGCCCAGGGGCACTCTCCATTCTCTT
rn      CATCCTCGTCCCAGTGTGTGGCCCTGTCAGGAGGTTTCCAGGGGCAGCCTCCATTCTCTT
cg      CATTGTCGTCGCAGTGTGTGGTCCTGTCAGGAAGTGCCCTGGAGCAGCCTCCATCTCTTC
        *     ******   ****      *  ****    * mm      CCTTGCTCAGTCATATGCCCTAGTTCTCTTGGAAGCCCTGGAGGACAGTGCTCACAGATC
rn      CCTTGCTCAGTCATATGCTCCAGTTCTCTTGGAAGCCCTGGAGGACAGTGTTCACAGACC
cg      CTCTGCTCAGTCATATTCCCCAGCTCTCTTGGAATCCCTGGAGATCAGTGTTCAGACACC
        *  *************  *   ******  ****      *  * *  * * mm      CCAAAGCCCCTTCCATTCTTATATCCCTCACCTAAGTTGCCCCGG-CTGCC---ACCTGT
rn      CCAAAGCCCCTTCCATTCTTAGACTCCTCACCTCAGTGGCCCTGG-CTGCT---ACCTGT
cg      CCAAAGCCGCTTCCGTTCTTACATCCCTGACCCTAGTTGCCCTGGGCTGCCTGCACCTGT
        ******  *  ****  *  * *   *    **       **** mm      GTTGGCTTGAGACTGACTGCCTCAGGCAGG----------------GGGGTGGTGAGAGA
rn      GTTGGCTTGAGGCTAGCTGCTTCAGGCAGGTAGTCTCCTGGCTCAGGGGATGGTGAGAGG
cg      GTTGGCT-AAGGCTAGCTGGTTCAGACAGG------------------------------
        *****     *  ** ** mm      ACTCTCTGCTATCAGCAGCACTGACTAGCCCCTCT--GTCAAACAGCTTCTTCTAGCCCA
rn      ACTCTCTGCTACCAGTAGCACTGAATAGCCCCTCT--GTCAAACAGCTTCT---AGCCCA
cg      ---------------CAGCACTGACTAGCCCCTCTCTGTCAAACAGCTTCTTCTAGCCCA
                       *****  **********  ********   **** mm      GTGATCAGTC
rn      GTGGTCAGTC
cg      GTGGTCAATT
        *** *** *
```

PROMOTER SEQUENCES

This application is the National Phase application of International Application No. PCT/EP2010/070537 with an international filing date of Dec. 22, 2010, and which claims priority on Application no. 09180432.8 filed with the European Patent Office on Dec. 22, 2009. The entire contents of all applications are incorporated herein by reference.

The present invention relates to regulatory and promoter sequences in isolated nucleic acids and expression cassettes.

Today, the majority of recombinant protein biopharmaceuticals are produced in mammalian cells. The Chinese Hamster Ovary (CHO) expression system is the dominant production platform for manufacturing such complex proteins. The cells can be grown to high cell densities in serum-free suspension cultures, enabling an easy scale-up in bioreactors, they are able to authentically process the desired proteins and they have got approval from regulatory authorities since the have a long history of safe use. In practice it is often difficult to obtain high yields of the recombinant product. Efforts to optimize mammalian expression systems are mainly focused on process and cell line improvement but another target for upstream process improvement makes up the genetic vector construct that has significant impact. For production purposes recombinant genes are usually transfected into the target cells as cDNA constructs in the context of a mammalian active expression cassette to allow transcription of the heterologous gene. The DNA construct is recognized by the cellular transcription machinery in a process that involves the activity of many trans-acting transcription factors (TF) at cis-regulatory elements, including enhancers, silencers, insulators and promoters. Intronless cDNAs usually yield low levels of transcribed mRNA in the cytoplasm since splicing and transport to the cytoplasm are functionally linked. In order to elevate the mRNA levels of the recombinant gene many vectors include an intron sequence that is generally located between the promoter and the cDNA insert.

The gene promoter is the key element and involved in all of these levels of regulation, serving as the determinant in gene transcription by integrating the influences of the DNA sequence, transcription factor binding and epigenetic features. It determines the strength and duration of transgene expression which is encoded by the plasmid vector. The most common promoters used for driving heterologous gene expression in mammalian cells are the human and mouse cytomegalovirus (CMV) major immediate early promoter, preferentially used with host cell systems such as CHO and NS0. They confer a strong short-term expression and have proved robust in several cell types including CHO and NS0. Their strong activity is due to the presence of multiple reiterations of several transcription factor binding sites within the promoter and upstream enhancer region. Other viral promoters such as the SV40 immediate early promoter and the Rous Sarcoma Virus (RSV) long-terminal-repeat (LTR) promoter are also used frequently in expression cassettes. As long as the transfer vector is in an episomal stage the construct is not subject to the same control mechanisms as an endogenous gene. After successful integration at a functional locus these viral promoters can account for constitutive high expression of the desired protein. However, this over-expression comprises a strong burden on cellular metabolism and the protein synthesis machinery and therefore can induce excessive stress reactions such as the unfolded protein response (UPR) or the ER stress response. These phenomena impair the correct processing of the recombinant proteins and may lead to induction of apoptosis. Another problem relates to cell-cycle dependence of these promoters, and the highest transcriptional activity is observed in the S-phase which leads to extreme cell to cell variation in the amount of recombinant protein expressed. In addition, these viral genetic elements are not part of the regulatory network of the host cell and often they are subject to gene silencing. In regard of public opinion and general biosafety concerns it also would be more acceptable to use non-viral promoters in expression cassettes instead of elements originating from viral sequences.

Some of these negative reactions could in principle be avoided if host-specific promoters and regulatory elements were used. Among the cell-specific best known promoters are those from house-keeping genes that encode abundantly transcribed cellular transcripts, such as beta-actin, elongation factor 1-alpha (EF-1alpha), or ubiquitin. Compared to viral promoters, insufficiently is known about many mammalian promoters, since eukaryotic gene expression is more complex and requires a precise coordination of many different factors. Although the activity of these promoters may be somewhat lower than that of the CMV promoter, their functional integrity within the cellular network is maintained. Also, they confer sustained transgene expression and long-term expression levels are more stable. A successful example represents the CHO-derived elongation factor-1 promoter (CHEF-1) that has been described for driving high-level expression in mammalian cells (WO 98/49289 A1). Another important aspect concerning the use of endogenous regulatory elements for transgene expression is the generation of stable mRNA and that expression can take place in the native environment of the host cell where trans-acting transcription factors are provided accordingly.

Since expression of eukaryotic genes is controlled by a complex machinery of cis- and trans-acting regulatory elements, most cellular promoters suffer from a lack of extensive functional characterization. A eukaryotic promoter is usually located immediately upstream of its transcribed sequence and serves as the point of transcriptional initiation. The core promoter immediately surrounds the transcription start site (TSS) which is sufficient to be recognized by the transcription machinery. The 'proximal promoter' comprises the region upstream of the core promoter and contains the TSS and other sequence features required for transcriptional regulation. Transcription factors act sequence-specific by binding to regulatory motifs in the promoter and enhancer sequence thereby activating chromatin and histone modifying enzymes that alter nucleosome structure and its position which finally allows initiation of transcription. The identification of a functional promoter is mainly dependant on the presence of associated upstream or downstream enhancer elements. On average, the sequence −300 to −50 nucleotides of the TSS positively contributes to core promoter activity and putative negative elements often are located 1000 to 500 base pairs upstream of the TSS. These characteristics largely determine the success of identifying a new promoter.

Alternative strategies to achieve high expression of the recombinant protein rely on an increased number of transgene copies and/or the protection of the recombinant construct from gene silencing. Depending on the applied methods of transfection and selective pressure, subclones with higher expression levels are generated. A central factor that influences and regulates gene expression is the dynamic structure of the cellular chromatin. Modification of the histones, which serves as an epigenetic marker for cellular events, activates additional enzymes and transcriptional regulators that can alter the chromatin structure and gene expression. For example, random integration into tightly packed and heavily methylated heterochromatin can lead to poor or no expression of the recombinant protein. These chromosomal elements which are located near the transfer vector integration site can lead to gene silencing, also known as position effect. One transcription promoting effect is mediated by insulators which are boundary elements that can shield genes from influences of their chromosomal environment and thereby prevent inactivation of the gene. Matrix attachment regions (MARs) or chromatin opening elements (UCOEs) are other motifs within the non-coding sequences of eukaryotic chromosomes which structurally organize the chromatin of the nucleus. They are capable of specific binding to nuclear proteins and they play an important role in the regulation of gene expression. All mentioned strategies for augmenting transcription levels of transgenes can further benefit when used in combination with newly identified cell-specific promoters. This can significantly reduce selection time and costs for recombinant clones due to screening a smaller number of transfectants and shorter cycling times required for gene amplification. These new regulatory elements have potential to increase the cell specific productivity and further enhance the performance of the system.

EBT Datenbank Acc. No. AC097705 provides a genomic sequence of *Rattus norvegicus* comprising a multitude of individual genes.

Kumar N. et al., BMC Biotechnology 8(42) (2008): 1-13 discloses a two dimensional gel electrophoresis experiment to identify differential protein expression in a temperature shift experiment in CHO cells, Genes GANAB, ALDH, DPYSL2, RBM3 and Vimentin were identified to be differentially expressed depending on culturing conditions and temperature.

Al-Fageeh M. et al., Biochem J 397 (2006): 247-259 relates to cold shock responses in mammalian and yeast cells.

Kaufmann H. et al., Biotechnology and Bioengineering 63(5) (1999): 573-582 describes effects of reduced temperature on protein phosphorylation in CHO cells.

Zervos E. E. et al., J Surgical Res 135 (2006): 317-322 relates to differential expression assays in cancer.

Therefore, one goal of the present invention is to obtain new promoter sequences suitable for expressing recombinant genes in mammal cells with high expression levels and without the drawbacks mentioned above.

Therefore, the present invention provides an isolated nucleic acid molecule comprising a sequence of Seq ID No: 1 or fragments thereof, said fragments having promoter activity or comprising a sequence having at least 70% identity to said sequence of Seq ID No: 1 or fragments thereof, or comprising a sequence that hybridizes to said sequence of Seq ID No: 1 or fragments thereof under stringent conditions. The invention has surprisingly found that also fragments of the inventive promoter sequence of Seq. ID No: 1 are active. Thus provided are also nucleic acid molecules comprising a promoter sequence of nucleotide (nt) 579 to nt 800 of SEQ ID NO:1, or comprising a sequence having at least 70% identity to said promoter sequence, or comprising a sequence that hybridizes to said promoter sequence under stringent conditions. These sequences of the nucleic acid molecule usually facilitate gene promoter activity (thus also referred to as "promoter sequences"). The term "promoter" refers to a sequence of DNA that functions to direct description of a gene product, e.g. encoding a recombinant protein, that is operably linked thereto. The promoter may or may not include control sequences such as transcriptional or translational regulatory sequences, involved in the expression of a given gene product. In general, transcriptional and translational regulatory sequences include but are not limited to the promoter sequence, may include the DNA response element for a transcriptional regulatory protein, ribosomal binding sites, transcriptional start and stop sequences, translational start and stop sequences, and enhancer or activator sequences. Usually a promoter also comprises one or more sequences to which transcriptional regulatory proteins bind ("DNA-binding protein"). Transcriptional regulatory proteins generally bind directly to such DNA response elements, however in some cases binding to DNA may be indirect by way of binding to another protein which in turn binds to, or is bound to the DNA response element.

The inventive Seq. ID. No: 1 has been isolated as a novel DNA sequence elements for controlling gene transcription in Chinese hamster ovary (CHO) and other mammalian host cells. Described sequences can function as transcriptionally active promoter elements and enable the expression of transiently or stably expressed genes.

The invention describes the identification and application of new mammalian DNA-sequence elements that can replace conventional viral promoters currently used in most eukaryotic expression vectors. The main advantage of the invention is the ability to permit gene expression to a higher level as compared to e. g. the viral SV40 promoter by using cell-specific, autologous cis-acting regulatory elements.

An advantage of endogenous promoters is their embedment and functional integrity within the host cellular network. Therefore, they confer robust transgene and stable long-term expression levels and many of the described problems observed with current mammalian expression cassettes can be prevented. Transcription takes place in the natural environment of the host cell which generates a stable recombinant mRNA and consequently trans-acting transcription factors are provided correctly.

It was surprisingly found that the inventive Seq. ID No: 1 and its related homologous sequences as well as its active fragments, in particular the promoter sequence portion of nt 579 to nt 800 of SEQ ID NO:1 or nt 579 to nt 910 of SEQ ID No: 1, have a temperature dependent gene promoter activity. In particular the inventive nucleic acid molecules can have conditionally inducible gene expression at reduced temperature that results in significantly augmented gene transcription levels compared to basal activity at standard temperature. Such a temperature dependent activity can be particularly advantageous to control activity of the cell at certain stages during the expression of recombinant proteins. It can be desirable to reduce expression at an initial phase during a cell culture to e.g. multiply the cells and at a later production phase to increase expression of the recombinant gene. This can be facilitated by a temperature shift towards lower temperatures by using the inventive promoters. It is particularly advantageous that this increase of productivity is achieved in low temperature culturing conditions which normally reduces overall cell metabolism of e.g. competitive processes but surprisingly not the expression of coding sequences operably linked to the inventive promoter sequences.

A "promoter" or a "sequence having promoter activity" is a region of DNA that facilitates the transcription of a particular gene. Transcription is process of generating a RNA of the gene or coding sequence of the gene during gene expression. the Transcription can be easily estimated, e.g. experimentally in test expression cell lines such as CHO cells, by determining the expression of a coding sequence of a gene operably linked to the promoter. Promoter sequences can be tested in luciferase reporter assays. The promoter of the present invention can act to modulate the expression of any such coding sequence of any gene. Thus the present invention also relates to chimeric genes, comprising any promoter sequence of the present invention operably linked to any coding sequence to be expressed. The promoter may be temperature sensitive, i.e. the amount of generated transcripts and/or expressed gene products is modified by temperature. The inventive promoters may have increased gene expression activity when the temperature is decreased below 37° C. In preferred embodiments the expression differs by a factor of at least 1.2, preferably at least 1.4, in particular preferred at least 1.6, between expression at 37° C. and 33° C.

As used herein, the terms "operably linked" or "operably positioned" relative to a gene product or coding sequence, e.g. in an expression cassette, means a sequence having promoter activity of the invention is in a functional relationship with another nucleotide component of the nucleic acid molecule. For example, a promoter or enhancer is operably linked to a coding sequence if it affects the transcription of the coding sequence. Such an operable linkage can e.g. be by providing the inventive promoter on the same DNA molecule as the coding sequence for a gene (cis-acting). Particular preferred the promoter sequences are upstream of coding sequences, i.e. on the 5' position of the coding sequence. The promoter can e.g. be at least 1, at least 10, at least 30, at least 50, at least 100, at least 150, at least 200, at least 250, at least 300, at least 400, at least 500 nucleotides upstream of the coding sequence or directly adjacent. In combination thereto or independently therefrom the promoter sequence can be less than 5000, less than 4500, less than 4000, less than 3500, less than 3000, less than 2500, less than 2000, less than 1500, less than 1000, less than 750, less than 500, less than 250, less than 100 nucleotides upstream of the coding sequence. A preferred range is that the fragment of nt 579 to nt 800 of SEQ ID NO:1 or its homologue is 300 to 1000 nts upstream of a coding sequence.

A "fragment" is a sequence comprising a part of a complete sequence from which it derives, which does not comprise the entire sequence of the complete sequence. A fragment according to the present invention can comprise a promoter sequence of e.g. at least 100 nt (nucleotides), at least 120 nt, at least 140 nt, at least 160 nt, at least 180 nt, at least 200 nt, at least 220 nt or at least 240 nt, at least 260 nt, at least 280 nt, at least 300 nt, at least 350 nt or at least 400 nt, corresponding to the inventive sequences disclosed herein, in particular of SEQ ID NO:1 or its homologous sequences.

Possible applications for the invention comprise the development of high expressing cell lines which are based on non-viral gene promoters, in particular CHO cells, for producing recombinant proteins including biopharmaceuticals.

As is shown in the examples, promoter active sequences have been isolated from a library encoding CHO genomic DNA by colony hybridization using labeled probes of selected genes. The sequence typically originates from 5' upstream regions of the respective CHO gene. Promoter sequences can be tested in luciferase reporter assays. Such assays usually comprise placing the promoter in a functional relationship, e.g. 5' upstream as mentioned above, to a luciferase encoding sequence in an expression vector and transfecting suitable host cells, preferably CHO cells with this vector. An active promoter is able to direct expression of the luciferase enzyme which in turn can be detected by common methods. Preferably the promoter of the invention induces expression of the gene product at least 3 times above a background level of non-promoting sequences. Functional domains may be identified and characterized by constructing different truncation and deletion mutants. The described sequences were surprisingly additionally characterized by an ability to augment basal expression levels under a defined environmental condition, such as lower temperature, as preferred functional ability of the inventive sequences. The invention also provides vectors and hosts that utilize such promoters.

It has been found that not the entire Seq. ID No: 1 is necessary for the gene promoter activity. In fact, a fragment of nt 579 to nt 800 of Seq. ID No: 1 was highly active. Further fragments of Seq. ID No: 1 which are preferably comprised in the nucleic acid molecule according to the present invention are of nt 1 to nt 1505 (complete Seq. ID No: 1), nt 1 to nt 1334, nt 1 to nt 1294, nt 1 to nt 1206, nt 1 to nt 910, nt 1 to nt 763, nt 450 to nt 1167, nt 450 to nt 1425, nt 115 to nt 910, nt 231 to nt 910, nt 450 to nt 910, nt 579 to nt 910, nt 1 to nt 800, nt 450 to nt 800, nt 115 to nt 800, nt 231 to nt 800, nt 450 to nt 800, and of course, nt 579 to nt 800 of Seq. ID No: 1. Particular preferred promoters of the inventive nucleic acid molecule are illustrated in Tables 4 and 6. Any inventive promoter sequence fragment of Seq. ID No: 1 may start at position 1, 115, 231, 344, 450 or position 579. The fragments may be up to nucleotides 763, 800, 910, 1167, 1206, 1294, 1334, 1425, 1505 of Seq. ID No: 1 or any combination thereof. These sequences are subsequently referred to as promoter sequences. Further preferred fragments which are provided according to the present invention, with 100% or at least 70% identity as further described herein, which are of SEQ ID NO 2 or 3 and correspond to these fragments listed above for SEQ ID NO 1. Such "corresponding" fragments or fragment positions in a nucleic acid molecule can be determined by sequence alignment programs such as Clustal W, preferably using default parameters. Such a sequence alignment is depicted in FIG. 4B.

The present invention further relates to homologous sequences to these inventive promoter sequences of Seq. ID No: 1 and its fragments which have at least 70% identity to any one of these promoter sequences. In preferred embodiments these sequences may have at least 75% identity, at least 80% identity, at least 85% identity, more preferred at least 90% identity, at least 95% identity, at least 98% identity, at least 99% identity or 100% identity to said promoter sequences. Such homologous sequences are e.g. SEQ ID NO 2 and 3 (FIG. 4B). Also provided are homologous sequences or fragments which have at least 60% or at least 65% identity to any one of the inventive promoter sequences when active.

Further homologous sequences are sequences that hybridize to said promoter sequences under stringent conditions (or to their complementary strands thereof to preserve the sequence relationship to the sequence of the fragments of Seq. ID No: 1 itself). Stringent conditions may include washing at about 65° C. in a buffer containing about 2×SSC and about 0.1% SDS or equivalent conditions.

These homologous sequences, deviating sequences with at least 70% identity, or hybridizing sequences, can relate to any one of the inventive promoter sequences (fragments of Seq. ID No: 1 or the complete Seq. ID No: 1). Preferably, the 70% identity or the hybridization is measured in comparison to nucleotides 579 to nt 800 of Seq. ID No: 1 or any of the above mentioned nucleotide ranges, e.g. nt 1 to nt 1505, nt 1 to nt 1334, nt 1 to nt 1294, nt 1 to nt 1206, nt 1 to nt 910, nt 1 to nt 763, nt 450 to nt 1167, nt 450 to nt 1425, nt 115 to nt 910, nt 231 to nt 910, nt 450 to nt 910, nt 579 to nt 910, nt 1 to nt 800, nt 450 to nt 800, nt 115 to nt 800, nt 231 to nt 800, nt 450 to nt 800, and of course, nt 579 to nt 800 of Seq. ID No: 1.

Sequence identity relates to nucleic acid sequence identity between two or more sequences, when aligned using a sequence alignment program. The reference to measure the sequence identity is Seq. ID No: 1 or its fragments as mentioned above. The sequence may comprise a deviation or modification from these inventive promoter sequences, in particular a nucleic acid mutation, in particular a nucleic acid substitution, addition or deletion. Sequence searches are preferably carried out using the BLASTN program when evaluating the % identity of the given nucleic acid sequence relative to a nucleic acid sequences of homologous promoters. BLASTN can e.g. be run using default parameters with an open gap penalty of 11.0 and an extended gap penalty of 1.0 and utilizing the blosum-62 matrix.

The nucleic acid molecule of the present invention can be DNA or RNA or a combination thereof such as mixtures or hybrid nucleic acids. In further preferred embodiments the nucleic acid molecule is isolated and/or purified.

The nucleic acid molecule may further comprise additional regulatory elements, e.g. enhancers, suppressors or isolators operably linked to the inventive promoter or to a coding sequence which is operatively linked to inventive sequences having gene promoter activity. Gene expression can be further modified by additional elements. Preferably these elements are inducible, such as by temperature shifts or certain chemicals to increase control of gene expression. Transcriptional enhancers are often located at a considerable distance from the relevant target promoters. Other types of enhancers may be located in the vicinity of a given promoter. In preferred embodiments nucleic acid molecules comprises a TATA-box element, in particular preferred a sequence portion of the sequence TATAA. Also preferred is a nucleic acid molecule of the present invention comprising a NF-κB binding element, in particular preferred comprising a sequence portion of the sequences TGGACAGTCC (SEQ ID NO: 41), GGGACGTCC or GGGACAGTCC (SEQ ID NO: 42). Further preferred is the presence of at least one Sp1 binding element in the nucleic acid molecule of the invention, preferably a sequence portion of the sequences GGGCGT or GGGCGG. Even more preferred embodiments the nucleic acid molecule comprises two or more of such Sp1 binding sites. In further preferred embodiments the nucleic acid molecule of the invention comprises one, two or more sequences or fragments thereof having promoter activity. By repetition of the inventive promoter sequences an increase of the activity is possible.

In preferred embodiments nucleotide portions adjacent to the inventive sequences are rich in GC with a content of G and C of at least 51%, at least 52%, or at least 53%, preferably at least 54%, preferably at least 55%, in particular preferred at least 56%, at least 57% or at least 58%, over an area of e.g. 10 nucleotides, 20 nucleotides, 30 nucleotides, 40 nucleotides, 50 nucleotides, or more. Adjacent nucleotides can be e.g. within 50, or within 100, or within 200, or within 300, or within 400 nucleotides to the inventive sequences having gene promoting activity. In cases of homologous sequences which have a certain sequence identity, e.g. at least 70% identity, to the inventive promoter sequences of Seq. ID No 1 or its fragments, or hybridizing sequences may also have additional sequences being GC-rich content, preferably comprising at least 51%, preferably at least 52%, at least 53%, at least 54%, at least 55%, at least 56%, at least 57%, or at least 58%, G and C. Although a high GC content may be significant for promoter activity it is preferred that modifications of the inventive promoter sequences are tested with the disclosed test systems. In particular it seems no universally required element within promoters are usually necessary for promoter activity there is a high possibility to vary the inventive sequences and still retain promoter activity.

In a second and third aspect of the present invention promoter sequences based on SEQ ID NO 2 and 3 are provided. SEQ ID NO 2 and 3 provide homologous sequences to the inventive SEQ ID NO 1 with similar structural elements and/or activities. The above description and preferred embodiments for SEQ ID NO 1 thus also apply for SEQ ID NO 2 an SEQ ID NO 3. E.g. the invention thus provides an isolated nucleic acid molecule comprising a sequence of SEQ ID NO 2 or 3 or fragments thereof, said fragments having promoter activity or comprising a sequence having at least 70% identity to said sequence of SEQ ID No 2 or 3 or said fragments thereof, or comprising a sequence that hybridizes to said sequence of SEQ ID NO 2 or 3 or said fragments thereof under stringent conditions, wherein the sequences have promoter activity.

Preferably the inventive nucleic acid is provided in a form suitable for easy handling, e.g. being of limited length. The nucleic acid molecule may thus exclude genomic sequences or large genomic fragments. In preferred embodiments the nucleic acid molecule comprises up to 30,000 nts (nucleotides), up to 25,000 nts, up to 20,000 nts, up to 15,000 nts, up to 12,500 nts, up to 10,000 nts, up to 9,000 nts, up to 8,000 nts, up to 7,000 nts, up to 6,000 nts. In preferred embodiments the nucleic acid molecule is flanked by endonuclease restriction sites at its 5' and/or 3' terminus.

In a further embodiment of the present invention an expression cassette is provided which comprises a sequence of a nucleic acid as defined above and a sequence of a gene product (i.e. a coding sequence) wherein the sequence of the invention is operatively positioned for expression of the gene product. The expression cassette may also be isolated and/or purified. Such expression cassettes may e.g. be provided in a vector suitable for transfection of a host cell. Also, the expression cassette may be provided in a modified genome of a host cell. The genome can e.g. be modified by recombinant techniques, in particular knock-in procedures or providing an artificial chromosome.

Preferably the inventive expression cassette is provided in a form suitable for easy handling, e.g. being of limited length. The expression cassette may thus exclude genomic sequences or large genomic fragments. In preferred embodiments the expression cassette comprises up to 30,000 nts, up to 25,000 nts, up to 20,000 nts, up to 15,000 nts, up to 12,500 nts, up to 10,000 nts, up to 9,000 nts, up to 8,000 nts, up to 7,000 nts, up to 6,000 nts. In preferred embodiments the expression cassette is flanked by endonuclease restriction sites at its 5' and/or 3' terminus.

In further preferred embodiments the expression cassette comprises intron sequences which are not translated and excised between transcription and translation. Such intron sequences may e.g. be located between a promoter sequence and a start codon of a coding sequence or within the coding sequence. It has been found that such intron sequences can increase gene expression due to a mechanistical relationship with transcript processing.

In a further aspect of the invention a vector is provided comprising a sequence of a nucleic acid molecule as defined above. The vector may also comprise the expression cassette as mentioned above. It can be isolated and/or purified. Preferably the vector is a biological functional vector such as an expression vector.

The inventive sequence having gene promoter activity is preferably positioned flanking an endonuclease site. This allows easy cloning of coding sequences into this vector operatively linked to the inventive sequences with promoter activity.

In a further aspect the inventive acid molecules, the expression cassettes or the vectors can be used for the expression of a gene product. One example is a method of expressing a gene product, preferably a protein, comprises transfecting an isolated cell or cell line in an expression cassette according to the invention and expressing the gene product, optionally further comprising isolating the expressed gene product.

A suitable host cell for expressing a gene product are e.g. mammal, avian, plant or insect cells. Preferably the cells are eukariotic. In particular preferred embodiments the cell is a cell of a rodent such as a mouse or rat and preferably a hamster cell. The cell can be of any tissue, preferably an ovarian cell, in particular a CHO cell. For single cell expression systems, preferably the cells are of a continuous cell culture.

In the further embodiment the invention relates to a cell obtainable by such a method as well as a cell comprising an nucleic acid molecule or an expression cassette or a vector as defined above. In preferred embodiments the nucleic acid, expression cassette or vector is stably integrated into the genome of said cell. Alternatively, it is also possible to incorporate these nucleic acids, expression cassettes or vectors transiently. A further aspect of the invention relates to a nucleic acid molecule comprising a sequence complementary to one of the inventive sequences having gene promoter activity. Such a complementary molecule usually binds to the inventive sequence. Such complementary sequences can be e.g. used to stably bind the inventive sequence having gene promoter activity to e.g. control expression of a gene. Upon stable binding of such a complementary sequence, expression may be enhanced or suppressed, in particular suppressed. The nucleic acid molecule with the complementary sequence may be of any nucleotide type, preferably nucleotide types which strongly bind to a DNA molecule with the inventive sequence having promoter activity. Such nucleic acid types with high binding ability are e.g. RNA, LNA (locked nucleic acids), or PNA (peptide nucleic acids).

The present invention further relates to a method of controlling expression of a gene product by an expression cassette as defined above, comprising administering to a cell with the expression cassette a nucleic acid molecule with a complementary sequence as mentioned above.

The present invention further relates to a method of controlling expression of a gene product by an expression cassette according to the invention in a cell comprising modifying the temperature of said cell. Usually the cells used for expressing a gene, in particular mammal cells, are cultured at 37° C. It was surprisingly found that the inventive promoter sequences are temperature sensitive, and are suitable to increase gene expression activity when the temperature is decreased below 37° C. To modify the temperature the temperature may e.g. be regulated below 36° C., below 35° C., below 34° C. or below 33° C. Preferably the temperature is at least sufficient to sustain viability of the cells and metabolism, e.g. at least 10° C., at least 12° C., at least 15° C., at least 17° C., at least 20° C., at least 22° C., at least 24° C., at least 26° C., at least 28° C., at least 30° C.

The present invention is further illustrated by the following figures and examples without being limited thereto.

FIGURES

Figure 3:
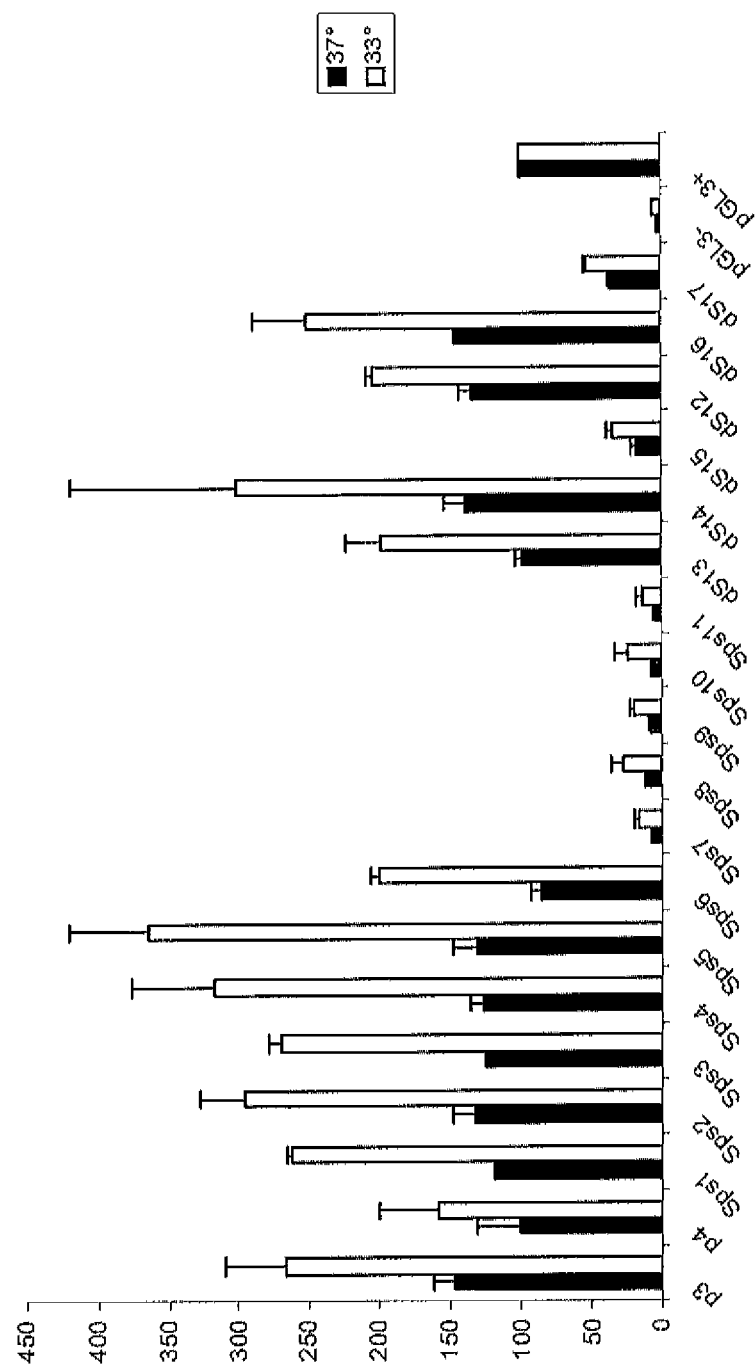

FIG. 1: Size of 3' flanking UTR of the CHO S100a6 gene encoded in lambda clone between T7 and B/D primer sites;

FIG. 2A: 5' Non-translated sequence region of the CHO S100a6 gene comprising 1505 nucleotides upstream the ATG start codon;

B: *Mus musculus* s100 calcium binding protein A6, 1-1505 by upstream of the ATG start codon;

C: *Rattus norvegicus* s100 calcium binding protein A6, 1-1505 by upstream of the ATG start codon;

FIG. 3: Normalized luciferase expression values of all promoter constructs at 37° C. and 33° C. 24 hrs post transfection;

FIG. 4 A: 5'-untranslated sequence alignment of the S100a6 gene among mouse (SEQ ID NO: 43), rat (SEQ ID NO: 44) and Chinese hamster (CHO) (SEQ ID NO: 45). NF-κB, two Sp1 binding sites and a TATA box sequence are indicated;

B: Multiple Sequence Alignments CLUSTAL W (1.81)
Sequence 1 (SEQ ID NO: 1): CHO (cg) 1505 bp
Sequence 2 (SEQ ID NO: 2): mouse (mm) 1505 bp
Sequence 3 (SEQ ID NO: 3): rat (m) 1505 bp
Sequences (1:2) Aligned. Score: 76
Sequences (2:3) Aligned. Score: 86
Sequences (1:3) Aligned. Score: 73

Figure 5:
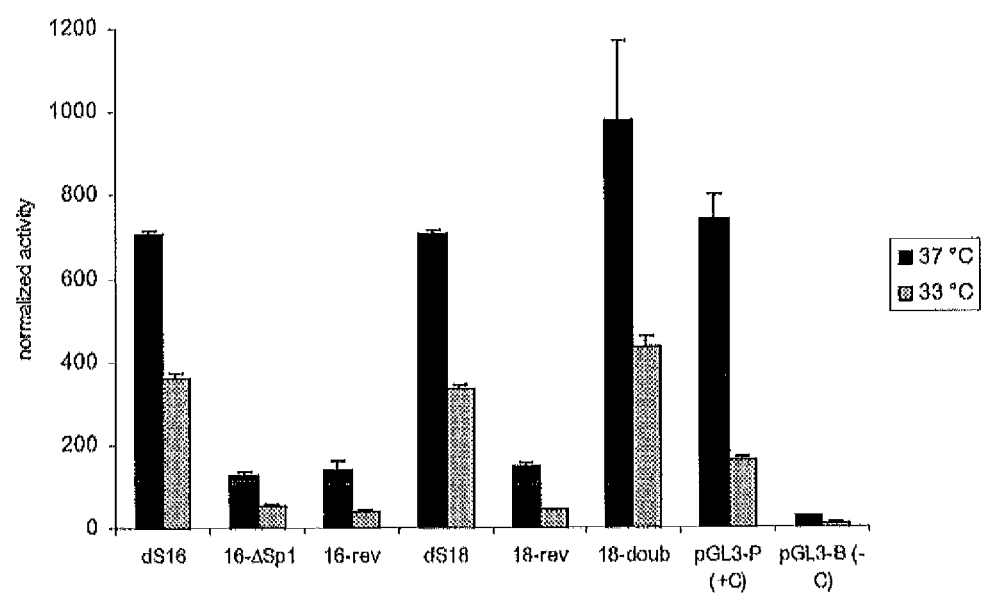
Figure 6:
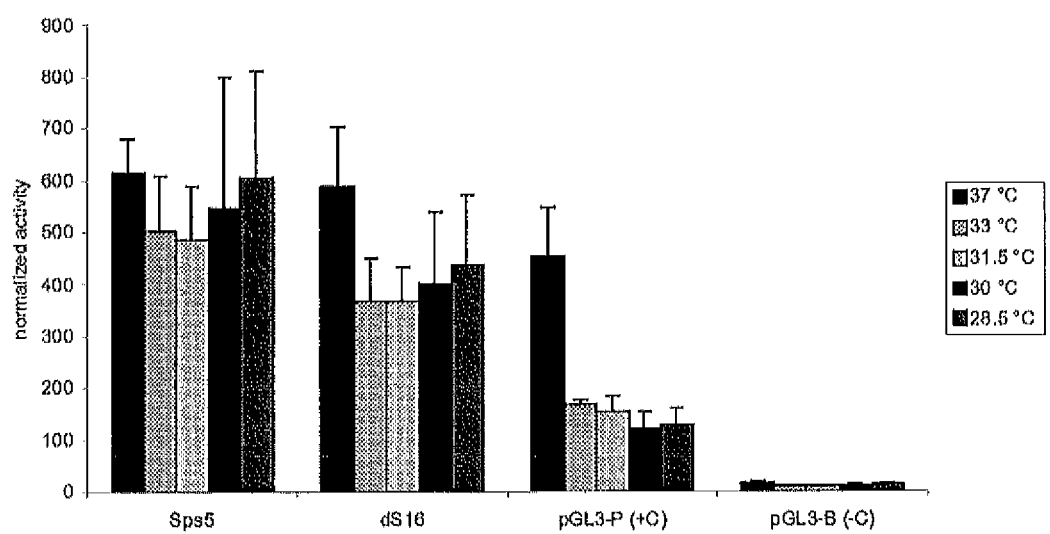

FIG. 5: Luciferase activity of 5 different constructs of the S100a6 promoter compared to dS16, +C (pGL3-P: positive control) and −C (pGL3-P: negative control). Lucifearse activity was measured 24 hours after transfection from 37° C. and 33° C. samples. All relative luciferase activities were normalized to Renilla luciferase activity. The average of two independent experiments with triplicate samples is shown for each construct;

FIG. 6: CHO cell lysates were measured for lucifearse activity 24 hours after transfection. Luciferase activities were normalized to Renilla luciferase values. The average of four independent experiments, each with triplicate samples, is shown for each construct.

EXAMPLES

For identifying promoter candidates global expression profiles were investigated and with focus on highly abundant transcripts that are constitutively expressed. These data were obtained from cross-species microarray gene expression results of various CHO clones that were cultivated under different conditions. A collection of about 80 different samples was analyzed to guarantee a representative number of experiments. Levels of transcript abundance were assessed according to the average signal intensity of each gene. A priority list of all candidate transcripts then was generated using a computational method that allows the prediction of eukaryotic promoters on a genomic scale. The Orthologous Mammalian Gene Promoter (OMGProm) database is a tool for searching a collection of known human and mouse orthologous gene promoters that are obtained from sources including GenBank, DBTSS, Ensembl, dbEST and Ref Seq. The availability of orthologous gene sequences enables cross-species comparison to identify core regions that are conserved across species. Orthologous sequence elements between human and mouse will likely have a better chance to show the same function also in CHO since transcriptional regulation is an evolutionarily conserved mechanism. Once a candidate sequence is identified deletion analyses on suspected promoter regions are performed in plasmid constructs and transfecting them into cultured host cells in vitro. This experimental method was also employed in order to characterize isolated sequences. In addition, differential gene expression in CHO cells was studied at lower temperatures (33° C.) and compared to standard cultivation temperature (37° C.). From these data several genes were selected with expression levels at least 1.5-fold higher than the control. Genes with high expression level prior to temperature reduction were preferentially analyzed.

Genomic sequence identification was achieved by screening a lambda phage library (Stratagene) encoding CHO genomic DNA fragments between 9 kb and 23 kb in size. DNA regions spanning upstream and downstream the translation start signal (TSS) were isolated using gene specific labeled probes.

Example 1

In Silico Evaluation of Promoter Candidates

Orthologous Mammalian Gene Promoters (OMGProm) database was used to search for promoter motifs and putative transcription start sites in a 2 kb upstream region of human and mouse orthologous genes. This cross-species comparison was done to identify conserved regions with similar functions and DNA sequence homology to the corresponding CHO sequence of the S100a6 gene (S100 calcium binding protein A6, calcyclin, Agilent ID: A_51_P281089; genebank: NM_011313; Gene ID: 20200).

Example 2

Screening of a CHO Genomic Library

A CHO-K1 genomic library in Lambda FIX II vector (Stratagene Inc, La Jolla, Calif.) was screened with a cDNA probe encoding Chinese hamster S100a6 gene. The cDNA sequence with a size of 256 base pairs was amplified with SuperScript® III Reverse transcriptase (invitrogen) and the use of primers S100B (5'-ATGGCATGCCCCCTG-GATCAG-3') (SEQ ID NO: 4) and S100F (5'-CATTGTA-GATCAAAGCCAAGG-3') (SEQ ID NO: 5). RT reaction was performed using 250 ng of CHO total RNA in a volume of 20 µl. Two microliters of the reaction product were further amplified by a PCR run at 98° C. for 30S for initial denaturation, 34 cycles of 98° C. for 10 s, 60° C. for 30 s and 72° C. for 15 s followed by a final extension at 72° C. for 5 min using Phusion DNA polymerase (Finnzymes) and primers S100B and S100F. The amplified RT-PCR product was gel-purified, sequenced and 100 pg were labeled with DIG-dUTP in one labeling reactions with a final volume of 50 µl using PCR DIG Probe Synthesis Kit (Roche). All cloning procedures were performed as described by (Sambrook and Russel 2001; page 1.84-1.97, 1.119-1.122, 5.4-5.17 and 8.1-8.53), restriction enzymes and other modifying enzymes were purchased from New England Biolabs (NEB, USA) and used as per the manufacturer's recommendations.

For one dish (145 mm) that was used for screening and plaque hybridization, fresh *Escherichia coli* XL1-Blue MRA (P2) (600 µl of OD600=0.5 cells diluted with 10 mM MgSO4) were infected with 10 µl of 50,000 plaque-forming units for 20 minutes at 37° C. Then 7 ml of NZY top agar at ~50° C. was added, mixed and spread onto a prewarmed (37° C.) NZY agar plate. The plaques became visible after 8 hours incubation at 37° C. After plaque formation, the culture dishes were stored at least 2 hours at 4° C., blotted on nylon membrane (Roche), denatured and neutralized. The step from preparing the plating cultures and performing the plaque lifts were done according to the instruction manual for Lambda FIX II Library (Stratagene).

Before hybridization, the DNA was fixed to the nylon membrane by baking at 80° C. for 2 hours. Prehybridization (39° C. for 1 hour) and hybridization (39° C. for overnight) were performed in the same solution, standard buffer (5×SSC, 0.1% (w/v) N-lauroylsarcosine, 0.02% (w/v) SDS and 1% blocking reagent). Ten milliliters of standard buffer containing 10 µl of DIG-labeled PCR product probe were used for hybridization for one nylon membrane. Membranes were washed twice with low stringency wash buffer (2×SSC, 0.1% SDS) at room temperature followed by high stringency wash buffer (0.5×SSC, 0.1% SDS) at 65° C., After washing and blocking, the antibody solution (1:10,000 diluted Anti-Digoxigenin-AP (Roche) in blocking solution) was added to the membrane to let the antibody bind to the DIG labeled probe. Membranes were washed, equilibrated, covered with CDP-Star (NEB) and exposed to Lumi-Imager (Roche) to detect with a chemiluminescent assay. All steps after performing the plaque lifts were done according to the DIG application manual (Roche).

The true-positive clone was confirmed by a second and third screening step. A square area of agar corresponding to the location of positive clone from the first screening was picked and used for a second screening. Then the positive clones were picked again using 1 ml pipette tip. In the last screening step, a probe encoding the 2nd exon sequence of S100a6 gene was also used. It was 135 base pairs in size and synthesized by the use of primers S2exB (5'-ATGGCATGC-CCCCTGGATCAG-3') (SEQ ID NO: 6) and S2exF (5'-GCCAATGGTGAGCTCCTTCTG-3') (SEQ ID NO: 7). Purification of lambda DNA of the positive clone was done with a Lambda kit (Qiagen Inc) and then the DNA was used in PCR reactions with T3, T7 and several S100a6 gene specific primers (for details see Table 1) for checking the presence and location of the gene. The lambda DNA was sequenced by GATC Biotech.

TABLE 1

Sequence of the primers used to confirm the presence and location of S100a6 in the lambda vector

| Primer | sequence (5'-3') | Direction/location of primer |
|---|---|---|
| A | CTCCTTTGGCTCTTCGCTGTC | sense/exon 1 |
| B | ATGGCATGCCCCCTGGATCAG | sense/exon 2 |
| C | CCTTCTTGTGGCCATCTTCC | sense/exon 2 |
| D | CTGAGATTGCAAGGCTGATGG | sense/exon 3 |
| E | GCCAATGGTGAGCTCCTTCTG | reverse/exon 2 |
| F | CATTGTAGATCAAAGCCAAGG | reverse/exon 3 |

Example 3: Promoter Constructs

According to the sequence information of the lambda DNA, two overlapping fragments of the 5' non-coding region of the S100a6 gene were amplified by PCR. The fragments were produced by using 1 of the 2 sense primers: −1425B (5'-GATGATggtaccGGAAGAAGCGAGTTA-GACAG-3') (SEQ ID NO: 14) and −1167B (5'-GATGATg-gtaccTACGGTGTGAAGCAGCAGTG-3') (SEQ ID NO: 46) together with the reverse primer −450F (5'-GATGA-TaagcttAGACCCCAGTGTAGACCACC-3') (SEQ ID NO: 15). The PCRs were performed in a reaction volume of 50 µl containing 1x Phusion HF buffer, 0.2 mM of each dNTPs, 0.5 µM of each primer, 1 unit of Phusion DNA polymerase (Finnzymes) and 1 ng of lambda DNA as template. The T3 thermocycler was utilized at the following PCR cycling conditions: initial denaturation at 98° C. for 2 min, 30 cycles of 98° C. for 10 s, 60° C. for 15 s and 72° C. for 45 s followed by a final extension at 72° C. for 7 min. The amplified PCR products were cloned into pGL3-basic (Promega) at KpnI-HindIII sites creating pGL3-S3 and pGL3-

S4. The resulting constructs were sequenced to verify the correct insert sequence in the vector.

In order to locate the core promoter of S100a6 more precisely, a set of 5′ deletion constructs, spanning the ~1.5 kbp upstream region of the S100a6 gene, were generated by PCR with the use of reverse primer (−1)F together with 1 of 11 sense primers as listed in Table 2. The nucleotide number in the primers name is relative to the ATG start codon.

TABLE 2

Sequence of the primers used to produce the reporter vector constructs with 5′ serial deletions of the promoter sequence of S100a6.

| SEQ ID NO | primer | sequence (5′-3′) |
|---|---|---|
| | Sense primer | |
| 16 | (−1505)B | GATGATggtaccGCATGCTGGCTGGGCTGGG |
| 17 | (−1343)B | GATGATggtaccTGAGACAGGGTTTTATATAGCC |
| 18 | (−1294)B | GATGATggtaccGGATCAACCTACTGAGCTATAT |
| 19 | (−1206)B | GATGATggtaccCACAAGTATTTACACTGAGATTC |
| 20 | (−910)B | GATGATggtaccATGCCGGAGTCACGAGTCAC |
| 21 | (−763)B | GATGATggtaccAGAGGCGTGGAAAACTGAGG |
| 22 | (−683)B | GATGATggtaccACTCCTTGGGCGGGCCTC |
| 23 | (−663)B | GATGATggtaccGGATGCTAGCCGCTATAAGG |
| 24 | (−534)B | GATGATggtaccAGGTCGGCTCCTGGGCTGG |
| 25 | (−322)B | GATGATggtaccTAGGGCGGCTCCCCGAGT |
| 26 | (−256)B | GATGATggtaccTCGCAGTGTGTGGTCCTGTC |
| | Reverse primer | |
| 27 | (−1)F | GATGATaagcttAATTGACCACTGGGCTAGAAG |

Twenty five microlitres of PCR mixture contained 1× buffer #1, 0.2 mM of each dNTPs, 1 mM of MgCl2, 0.4 μM of each primer, 1 unit of KOD Hifi DNA polymerase (Novagen) and 1 ng of lambda DNA as template. The cycles were as follows: 95° C. for 2 min, 30 cycles of 98° C. for 15 s, 58° C. for 5 s and 72° C. for 20 s, final extension at 72° C. for 5 min. The 11 PCR products were cloned into pGL3-basic at KpnI-HindIII sites and sequenced. The resulting constructs were designated from pGL3-dSp1 to pGL3-dSp11 according to the size of deletion starting with the full-length construct derived with primer (−1505)B to the smallest obtained with primer (−256)B.

With a second set of 3′ deletion constructs the minimal promoter sequence which is absolutely required for full activity was determined. In previous experiments it was shown that the 5′ upstream sequence region beyond nucleotide position −910 relative to the ATG translation start codon is not essential for positively contributing to promoter strength. Several constructs were generated by PCR with the use of sense primer (−910)B together with 1 of the 7 reverse primers as listed in Table 3.

TABLE 3

Sequence of the primers used to generate the reporter vector constructs with 3′ serial deletions.

| SEQ ID NO | primer | sequence (5′-3′) |
|---|---|---|
| 28 | reverse primer | |
| | S-HindIII (−115)-F | GATGATaagcttTCAGGGATGTAAGAACG-GAAGC |
| 29 | S-HindIII (−231)-F | GATGATaagcttCTTCCTGACAGGACCACACAC |
| 30 | S-HindIII (−344)-F | GATGATaagcttGCTTGCCTGGCACAACCAAGC |
| 31 | S-HindIII (−461)-F | GATGATaagcttTAGACCACCCGCGGAACCCG |

TABLE 3-continued

Sequence of the primers used to generate the reporter vector constructs with 3' serial deletions.

| SEQ ID NO | primer | sequence (5'-3') |
|---|---|---|
| 32 | S-HindIII (-579)-F | GATGATaagcttGGCAGGTAGACAGCGAAGAGC |
| 33 | S-HindIII (-651)-F | GATGATaagcttGCGGCTAGCATCCGGGAGG |
| 34 | sense primer (-910)B | GATGATggtaccATGCCGGAGTCACGAGTCAC |

Example 4

Cell Culture and Transient Transfection Assay

Dihydrofolate-reductase deficient CHO-cells (ATCC; CRL-9096) were cultured in Dulbecco's modified eagle's medium (DMEM) and Ham's F-12 medium mixed in a 1:1 ratio (Invitrogen, Carlsbad, USA) supplemented with 4 mM L-glutamine, 0.1% (w/v) pluronic, 0.25% (w/v) soya-peptone, 13.60 mg/l of hypoxanthine and 3.88 mg/l of thymidine, at 37° C. under 7% CO2. The cells were routinely split 1:6 twice a week and used for transient transfection assays.

The constructed plasmids were transfected or co-transfected along with the Renilla luciferase reporter vector pRL-SV40 (Promega) into CHO dhfr-cells by using Amaxa's Nucleofector (Lonza). Cells were transferred to a 15 ml tube at the amount of 4×106 cells per one nucleofection sample and centrifuged at 1000 rpm for 10 min. After the supernatant was removed completely, cells were resuspended with the nucleofection mixture containing 10 µg of plasmid DNA, 1 µg of pRL-SV40 in 100 µl of Nucleofector™ solution. The sample was transferred into a cuvette and then it was subjected to the Nucleofector for electroporation. After transfection, the cells were transferred into prewarmed culture medium into 6-well plates and incubated at 37° C. or when necessary, the cells were mixed well before splitting to 1:1 in two 12-well plates and incubated at 33° C. and 37° C. for temperature shift investigation. The luciferase activities were measured on a Biotek Synergy 2 luminometer (Gen5 software) by using the Dual-Luciferase Reporter Assay System (Progema) according to the manufacturer's instructions preferentially after 24 hours and optionally at time points 48 or 72 hours post transfection. To normalize for transfection efficiency, the promoter activity of each construct was expressed as the ratio of firefly luciferase activity relative to Renilla luciferase activity. pGL3-Basic and pGL3-Promoter were used as the negative and positive vectors, respectively.

Example 5

Results

The promoter active sequence was identified by hybridization of the phage DNA to a DIG-labeled probe specific for the coding sequence of the CHO S100a6 gene. The DNA-sequence was enriched and purified from a single phage clone after three successive plaque screening rounds. The size of the inserted genomic fragment was determined by different PCR amplification steps using primer D specific for exon-3 and primer B specific for exon-2 (see Table 1) together with the T7 (5'-TAATACGACTCACTATAGGG-3') vector primer specific for the T7 promoter binding within the multiple cloning site of the lambda DNA. The results revealed the presence of about 6 kb of the 3' non-translated sequence of the CHO S100a6 gene (FIG. 1). The two specific bands are marked by arrows. Amplification reactions using antisense exon primers in combination with the T3 promoter primer did not yield a specific product, presumably due to the larger genomic flanking region at this site.

Example 6

Promoter Mapping and Dissection

Since the core promoter and additional sequences that positively contribute to promoter activity are usually located within 500 base pairs upstream the translation start signal, this region and a substantial larger fragment of the 5' non-translated sequence and various mutants thereof were investigated. The selected full-length sequences (SEQ ID NO 1-3) that are analyzed are shown in FIG. 2.

The S100a6 gene consists of three exons, of which exon-1 is non-translated. In exon-2 the ATG translation start codon is positioned at nucleotide 25 and translation is terminated at position 132 of exon-3 near the end of the mRNA sequence. The exons are interspaced by two introns, intron-1 which is 550 nucleotides in size and intron-2 which consists of 287 nucleotides. The structural organization of the CHO gene is similar to that of mouse and both, exon-2 and exon-3 are identical in size between hamster and mouse. The sequence homology of the coding region between mouse and CHO accounts for 94%, whereas the introns only show an average homology of 77%.

Two transcriptional start sites within the sequence in FIG. 2 are predicted by the Neural Network Promoter Prediction program (http://www.fruitfly.org/seq_tools/), one of which is located in exon-1 at position 620 upstream the ATG start codon and the second within intron-1 at position 420. In addition, the sequence in FIG. 2 comprises a region that incorporates a high frequency of CG-nucleotides as identified by the EMBOSS cpgplot program (http://www.ebi.ac.uk/emboss/) made available by the European Bioinformatics Institute (EBI) part of European Molecular Biology Laboratory (EMBL). The parameters that were used for the CpG island search were set to a GC-content of greater than 50% and an observed/expected CpG ratio that is greater than 60%. One putative island region of 170 nucleotides reaching from nucleotides 577 up to 747 relative to the ATG start signal was identified which overlaps with the exon-1 sequence. There are three predicted SP1 transcription factor binding motives present in the sequence, two within the CpG-island region and exon-1 at position 671-676 and 690-695 and a third site within intron-1 at nucleotides 315-320, upstream the ATG start codon.

Starting from the full-length sequence, deletion mutants were designed by successive removal of 5' and 3' nucleotides in order to identify transcription promoting activity in the flanking regions of the gene. In addition, the location and size of the minimal promoter region is determined and its expression strength in proportion to the entire sequence. The different promoter constructs are outlined in Table 4. Characters 5d and 3d in the name of the constructs indicate the site where the deletion was made. Numbers behind denote nucleotides that were truncated from the full length sequence. In the next column the size and the nucleotide position representing the region are shown for each construct. In the column to the right the length of each deletion construct is depicted in the table.

TABLE 4

Promoter constructs of S100a6 5' upstream region

| # | name | nt | length |
|---|------|-----|--------|
| p3 | 5d388.3d449 | 450-1167 | 718 |
| p4 | 5d80.3d449 | 450-1425 | 976 |
| Sps1 | 5d0 | 1-1505 | 1505 |
| Sps2 | 5d162 | 1-1334 | 1343 |
| Sps3 | 5d211 | 1-1294 | 1294 |
| Sps4 | 5d299 | 1-1206 | 1206 |
| Sps5 | 5d595 | 1-910 | 910 |
| Sps6 | 5d742 | 1-763 | 763 |
| Sps7 | 5d822 | 1-683 | 683 |
| Sps8 | 5d842 | 1-663 | 663 |
| Sps9 | 5d971 | 1-534 | 534 |
| Sps10 | 5d1183 | 1-322 | 322 |
| Sps11 | 5d1249 | 1-256 | 256 |
| dS13 | 5d595.3d114 | 115-910 | 796 |
| dS14 | 5d595.3d230 | 231-910 | 680 |
| dS15 | 5d595.3d343 | 344-910 | 567 |
| dS12 | 5d595.3d460 | 450-910 | 461 |
| dS16 | 5d595.3d578 | 579-910 | 332 |
| dS17 | 5d595.3d650 | 651-910 | 260 |

Example 7

Reporter Assays

All different promoter constructs were inserted into the promoter-less basic vector pGL3-B (basic) (Promega) between the KpnI-HindIII sites immediately upstream the reporter gene firefly luciferase. As control vectors the empty pGL3-B basic plasmid was used to determine the background levels in this assay. As positive control vector pGL3-Promoter (promoter) (Promega) was used that contains the viral Simian virus 40 (SV40) promoter and the same vector backbone. Quantitative reporter assays were done in co-transfection experiments in order to standardize experimental variations like transfection efficiency or differences in cell numbers between samples. As a second plasmid pRL-SV40 (Promega) which encodes the renilla luciferase gene under control of the SV-40 promoter was co-transfected along with all the promoter constructs under study and the appropriate control plasmids. Since the expression level of the renilla plasmid usually is higher as compared to firefly luciferase, only one tenth of the vector concentration was used. For measuring the luminescence signal of both reporter proteins the Dual-Glo assay was used which allows a consecutive measurements of both proteins from the same cell sample.

After the co-transfection, the cells were separated and transferred to 12-well plates to test for reporter gene expression at different temperatures. One set of plates was incubated at 37° C. and the other one at 33° C. 24 hrs after transfection, aliquots of each sample were prepared and quantitatively analyzed. The calculation of promoter activity was done by dividing the signal from firefly luciferase by that from renilla and after that the values were normalized to the corresponding pGL3-P positive control samples which were set to 100%. An overview of the activity of all promoter constructs is shown in FIG. 3.

In the first series of constructs 5' truncation mutants were designed to study the effect of a successive loss of essential regulatory elements like TATA-box and SP1 transcription factor binding sites which are present in the full-length constructs. The absence of predicted TATA-box motifs did not significantly influence the activity whereas loss of one out of the three SP1 binding sites dramatically reduced promoter function to almost background levels. Construct Sps6 encoding nucleotides 1 to 763 upstream of the ATG signal showed 80-90% reporter gene expression strength of the control vector. In contrast, construct Sps7 which encodes nucleotides 1 to 683 but lacks the essential Sp1 binding site, completely lost promoter functionality. The other truncation mutants Sps8 to Sps11 encoding 663 down to 256 nucleotides of the 3' end of the full-length sequence also did not exhibit functional activity. Construct Sps5 that includes 910 nucleotides of the 3' end shows an expression value that is considerably higher than the positive control and equally or even higher than the longer constructs extending down to nucleotide 1505. Therefore position 910 was selected as the starting point for designing 3' deletion mutants which includes Sps12 to Sps17 with varying length between 796 to 260 nucleotides. All constructs except the Sps17 and Sps15 showed promoter activity at least comparable to or up to 1.5-fold the value of the control. The drop in activity observed in the shortest construct Sps17 may be due to the absence of the putative TATA-box at position 324 or another critical region. Construct dS16 which comprises 332 nucleotides with 595 nucleotides deleted at the 5' site and 578 deleted at the 3' end of Sps1 was identified as the minimal promoter region. The promoter active sequence is located in exon-1 which also contains the putative CpG-island of 170 nucleotides. Its expression strength is among the top three of all constructs compared.

Promoter analyses under hypothermic conditions reveal an even higher factor of induction for all tested variants as compared to the control (Table 5). In general, reduced temperature caused a boost in expression of 200% on average. At 33° C., three of the 5' deletion constructs Sps4, Sps5 and Sps6 show a substantial enhancement in reporter gene expression of more than 2-fold when compared to the corresponding samples of the 37° C. culture. This corresponds to more than 300% of the non temperature sensitive SV40 control vector expression strength when measured under temperature shift conditions. Also the remaining 3' truncation constructs, Sps1 to Sps3 which all encode three SP1 transcription factor binding sites, can be constantly activated >2-fold upon a shift to 33° C. Out of these six constructs, Sps4 and Sps5 show the strongest response to temperature change.

All SP1 sites are located within the first seven hundred nucleotides of the non-translated region, two of which are present in exon-1 and one in the first intron (Table 5). The expression stimulating response at lower temperature is not so pronounced for the constructs Sps13, Sps14, p3 and p4. The two latter constructs are missing one SP1 site, but still show a factor of induction ranging between 1.57 to 1.81-fold of their 37° C. value. A successive reduction in temperature response was observed with decreasing length of the promoter sequence. Constructs Sps12, Sps16, and Sps17 are ranging between levels of 1.46 to 1.74-fold of their control values, with the lowest rate of temperature enhanced expression observed for construct Sps17 which encodes only 260 nucleotides of the promoter sequence and completely lacks intron-1 and one third of the first exon.

TABLE 5

Temperature induced expression increase

| # | te-1* | te-2* | AVE | SD | SP1** | nt |
|---|---|---|---|---|---|---|
| p3 | 1.74 | 1.89 | 1.81 | 0.11 | 3-2-- | 450-1167 |
| p4 | 1.60 | 1.53 | 1.57 | 0.05 | 3-2-- | 450-1425 |
| Sps1 | 2.22 | 2.18 | 2.20 | 0.02 | 3-2-1 | 1-1505 |
| Sps2 | 2.23 | 2.25 | 2.24 | 0.01 | 3-2-1 | 1-1334 |
| Sps3 | 2.10 | 2.24 | 2.17 | 0.10 | 3-2-1 | 1-1294 |
| Sps4 | 2.70 | 2.29 | 2.49 | 0.29 | 3-2-1 | 1-1206 |
| Sps5 | 2.26 | 3.36 | 2.81 | 0.78 | 3-2-1 | 1-910 |
| Sps6 | 2.25 | 2.48 | 2.37 | 0.16 | 3-2-1 | 1-763 |
| dS13 | 1.87 | 2.10 | 1.98 | 0.16 | 3-2-1 | 115-910 |
| dS14 | 1.70 | 2.57 | 2.14 | 0.61 | 3-2-1 | 231-910 |
| dS15 | 1.78 | 1.87 | 1.83 | 0.07 | 3-2-- | 344-910 |
| dS12 | 1.57 | 1.48 | 1.52 | 0.07 | 3-2-- | 450-910 |
| dS16 | 1.56 | 1.91 | 1.74 | 0.25 | 3-2-- | 579-910 |
| dS17 | 1.44 | 1.47 | 1.46 | 0.02 | 3-2-- | 651-910 |

*temperature effects (te) were analyzed in two independent measurement series (1 and 2). Numbers show the fold-change values at 33° C. as compared to 37° C., relative to the corresponding sample of the control vector pGL3-P.
**this column shows the number of SP1 transcription factor binding sites present in the respective construct. SP1-sites occur at positions 671-676, 690-695 and 315-320. Nucleotides encoded by individual constructs are shown in the far right column.

TABLE 6

Description of additional promoter constructs

| # | name | nucleotide | length |
|---|---|---|---|
| 16-ΔSp1 | 5d595.3d578, Δ784-847 | 579-658, 721-910 | 268 |
| 16-rev | 5d595.3d578 * | 579-910 | 332 |
| dS18 | 5d705.3d578 | 579-800 | 222 |
| 18-rev | 5d705.3d578 * | 579-800 | 222 |
| 18-double | 5d705.3d588, 5d714.3d578 | 589-800, 579-791 | 425 |

* The fragments were cloned in reverse orientation into the reporter vector.

To generate the minimal, reverse and double promoter constructs the primers listed in Table 7 were used. A reversely-oriented construct of dS16 (16-rev) was generated by cloning of the fragment amplified with the use of primers HindIII(−910)B and KpnI(−579)F into the pGL3-Basic vector. The minimal promoter construct was produced by removing 110 by upstream of the promoter sequence from dS16, yielding construct dS18. The insert for the dS18 construct was amplified by PCR using the primers KpnI(−800)B and (−579)F. Construct 18-rev was generated by PCR with the use of primers HindIII(−800)B and KpnI(−579)F and cloned into the vector in reverse orientation. To investigate the promoter activity of the core promoter sequence in two tandem repeats, the construct pGL3-18double was generated. Initially, two fragments of this promoter were cloned. The first sequence was amplified with KpnI(−800)B and XhoI(−589)F and the second fragment with XhoI(−791)B and (−579)F. The resulting PCR products were cut with corresponding enzymes and subsequently ligated together into pGL3-Basic vector. All fragments were cloned into pGL3-Basic at KpnI-HindIII sites and further sequenced to verify the authenticity of the inserts.

TABLE 7

Sequence of the primers used to produce the minimal, reverse and double promoter constructs.

| SEQ ID NO | Primer designation | Primer sequence (5'-3') |
|---|---|---|
| 35 | HindIII(-910)B | GATGATAAGCTTATGCCGGAGTCACGAGTCAC |
| 36 | KpnI(-579)F | GATGATGGTACCGGCAGGTAGACAGCGAAGAGC |
| 37 | KpnI(-800)B | GATGATGGTACCCCTCATGCCACTCCCAATCC |
| 38 | HindIII(-800)B | GATGATAAGCTTCCTCATGCCACTCCCAATCC |
| 39 | XhoI(-791)B | GATGATCTCGAGACTCCCAATCCGGGACAGTC |
| 40 | XhoI(-589)F | GATGATCTCGAGCAGCGAAGAGCCAAAGGAGTG |

Example 8

Active Shortened Promoter Sequence and Mutants Thereof

In further experiments several other constructs were generated (Table 6).

The smallest functional entity dS16 (579 to 910) of example 6 was further shortened by removing another 110 by from the 5' end, generating a truncated promoter construct (dS18) containing nucleotides 579 to 800 of the Sps1 full length sequence. In doing so a putative NF-κB transcription factor binding site which is located at position 780 to 771 of the promoter sequence is maintained. The NF-κB consensus motif is conserved among the S100a6 gene of Chinese hamster, mouse and rat (FIG. 4). Construct dS18 is comprised of 222 nucleotides including one NF-κB site, two Sp1 binding sites and a TATA box. The NE-κB binding site in dS18 is necessary for full promoter function since lacking of this site in Sps6 (1 to 763) results in reduced promoter activity (decrease to 65%) when compared to the Sps5 (1 to 910). Construct ds18's activity is similar to dS16 promoter (FIG. 5).

In addition, a deletion mutant of ds16 was generated (16-ΔSp1) to verify the necessity of two Sp1 transcription factor binding sites. The lack of only 64 bp, including two putative Sp1 binding sites in construct 16-ΔSp1 (579-658.deleted.721-910) dramatically decreased promoter function to about 20% (FIG. 5). This observation is relevant since the Sp1 site, a GC hexanucleotide, is sufficient for SV40 promoter activity and it frequently appears in multiple copies. A tandem repeat of two GC boxes stimulates transcription significantly more efficiently as a single element, and the distance of the Sp1 site(s) from the TA-TA box may be critical.

Some mammalian promoters have been shown to exhibit expression activity when used in antisense orientation, mainly as a consequence of the GC box's reverse function. Thus the function of the two versions of the S100a6 core promoter was investigated by reverse orientation of dS16 and dS18, resulting in the two constructs 16-rev and 18-rev. In quantitative reporter assays an activity of about 20% was detected for these two variants as compared to the full length sequence (FIG. 5).

Reiterations of core promoter elements are known to allow enhanced transcriptional activity when compared to single copy versions. Construct 18-double was generated to investigate the activity of two repeated core promoter sequences. Reporter assays of this promoter tandem repeat gave rise to improved promoter functionality since its activity was 1.4-fold more effective in comparison to the single copy construct dS18 (FIG. 5).

The temperature induced increase in expression at 33° C. was also observed for the two new constructs dS18 and 18-double and compared to that of ds16 (Table 8).

TABLE 8

| Temperature induced expression increase | | | | | |
|---|---|---|---|---|---|
| # | te-1 * | te-2 * | AVE | SD | nucleotide |
| dS16 | 2.50 | 2.19 | 2.35 | 0.15 | 579-910 |
| dS18 | 2.43 | 1.95 | 2.18 | 0.24 | 579-800 |

TABLE 8-continued

| Temperature induced expression increase | | | | | |
|---|---|---|---|---|---|
| # | te-1 * | te-2 * | AVE | SD | nucleotide |
| 18-doub | 2.05 | 2.10 | 2.04 | 0.03 | 589-800, 579-791 |

* Temperature effects (te) were analyzed in two independent measurement series (1 and 2). Numbers show the fold-change values at 33° C. as compared to 37° C., relative to the corresponding sample of the control vector pGL3-P.

Example 9

Temperature Down Shift Induction

S100a6 promoter variants Sps5 and dS16 were investigated under different hypothermic conditions at temperatures of 33° C., 31.5° C., 30° C., 28.5° C. and the reference temperature 37° C. Cell lysates were measured for luciferase expression 24 hrs after transfection. The result of this analysis is shown in FIG. 6.

Testing gene expression at lower temperatures was based on general findings that production of recombinant proteins in CHO cells can be enhanced by lowering the temperature.

As observed in several temperature shift experiments, the time point at which reporter gene activity is measured is critical, since this has great impact on the ratio between the 37° C.-sample and a lower temperature sample. Over time, low temperature cultures show a continuous increase in expression, presumably due to retarded metabolism and intracellular accumulation of the reporter protein. Therefore, the ratio of each construct at a given temperature to the control vector (pGL3-P) under identical conditions was calculated according to: expression of clone (n) at temp (k)/expression pGL3-P at temp (k). These specific values are shown in Table 9.

TABLE 9

| Temperature specific expression | | | | |
|---|---|---|---|---|
| temp(° C.) | # | FC* | # | FC* |
| 37 | Sps5 | 1.4 | dS16 | 1.3 |
| 33 | Sps5 | 3.0 | dS16 | 2.2 |
| 31.5 | Sps5 | 3.1 | dS16 | 2.4 |
| 30 | Sps5 | 4.4 | dS16 | 3.3 |
| 28.5 | Sps5 | 4.7 | dS16 | 3.4 |

*Fold change (FC) indicates the ratio of each construct at a given temperature to the control vector (pGL3-P) under identical conditions The results indicate the temperature dependence of both constructs which increases when temperature is decreased (compared to the SV40 promoter). This temperature effect is more pronounced in construct Sps5 comprising nucleotides 1-910 than in dS16 representing a much smaller portion of only 332 nucleotides.

The invention claimed is:

1. An expression cassette comprising:
a polynucleotide that is:
(i) a fragment of SEQ ID NO: 1, wherein the fragment comprises nt 579 to nt 800 of the sequence as set forth in SEQ ID NO:1;
(ii) a nucleic acid sequence having at least 90% identity to (i);
(iii) the nucleic acid sequence as set forth in SEQ ID NO: 1;
(iv) a nucleic acid sequence having at least 75% identity to (iii); or
(v) the complementary sequence of (i), (ii), (iii) or (iv); and
a heterologous coding sequence.

2. A vector comprising the expression cassette of claim 1.

3. A method of recombinantly expressing a protein gene product, the method comprising:

expressing in a cell a gene product from an expression cassette comprising a coding sequence and a nucleic acid sequence, wherein the coding sequence is heterologous to the nucleic acid sequence and wherein said nucleic acid sequence has promoter activity and is operatively positioned for expression of the coding sequence, and wherein said nucleic acid sequence comprises (i) the sequence as set forth in SEQ ID NO: 1 or (ii) a fragment of SEQ ID NO: 1, wherein the fragment comprises nt 450 to nt 800 or nt 579 to nt 800 of SEQ ID NO: 1.

4. A method of expressing a gene product, the method comprising transfecting an isolated cell or cell line with an expression cassette according to claim 1, wherein said polynucleotide has promoter activity and is operatively positioned for expression of the coding sequence, and wherein said polynucleotide comprises (i) the sequence as set forth in SEQ ID NO: 1 or (ii) a fragment of SEQ ID NO: 1, wherein the fragment comprises nt 450 to nt 800 or nt 579 to nt 800 of SEQ ID NO:1; and expressing the gene product, wherein, optionally, the method further comprises the step of isolating the expressed gene product.

5. The method of claim 4, characterized in that the cell is a mammal, avian, plant or insect cell.

6. An isolated cell comprising an expression cassette according to claim 1 wherein the expression cassette is stably integrated into the genome of said cell.

7. A non-human cell comprising a vector according to claim 2, wherein the vector is stably integrated into the genome of said cell.

8. A method of controlling expression of a gene product by an expression cassette in a cell, comprising modifying the temperature of a cell that comprises the expression cassette according to claim 1, wherein said polynucleotide has promoter activity and is operatively positioned for expression of the coding sequence, and wherein said polynucleotide comprises (i) the sequence as set forth in SEQ ID NO: 1 or (ii) a fragment of SEQ ID NO: 1, wherein the fragment comprises nt 450 to nt 800 or nt 579 to nt 800 of SEQ ID NO: 1.

9. The expression cassette of claim 1, wherein the fragment comprises nt 1 to nt 1334, nt 1 to nt 1294, nt 1 to nt 1206, nt 1 to nt 910, nt 450 to nt 1167, nt 450 to nt 1425, nt 115 to nt 910, nt 231 to nt 910, nt 450 to nt 910, nt 579 to nt 910, nt 1 to nt 800, nt 450 to 800, nt 115 to nt 800, nt 231 to nt 800, or nt 450 to nt 800 of SEQ ID NO:1.

10. The expression cassette of claim 1, wherein the nucleic acid sequence of (iv) has at least 80% sequence identity to the sequence set forth in SEQ ID NO: 1.

11. The expression cassette of claim 1, wherein the nucleic acid sequence of (iv) has at least 90% sequence identity to the sequence set forth in SEQ ID NO:1.

12. The expression cassette of claim 1, wherein the nucleic acid sequence of (iv) has at least 95% sequence identity to the sequence set forth in SEQ ID NO:1.

13. The vector of claim 2, wherein the fragment comprises nt 1 to nt 1334, nt 1 to nt 1294, nt 1 to nt 1206, nt 1 to nt 910, nt 450 to nt 1167, nt 450 to nt 1425, nt 115 to nt 910, nt 231 to nt 910, nt 450 to nt 910, nt 579 to nt 910, nt 1 to nt 800, nt 450 to 800, nt 115 to nt 800, nt 231 to nt 800, or nt 450 to nt 800 of SEQ ID NO:1.

14. The vector of claim 2, wherein the nucleic acid sequence of (iv) has at least 80% sequence identity to the sequence set forth in SEQ ID NO:1.

15. The vector of claim 2, wherein the nucleic acid sequence of (iv) has at least 90% sequence identity to the sequence set forth in SEQ ID NO: 1.

16. The vector of claim 2, wherein the nucleic acid sequence of (iv) has at least 95% sequence identity to the sequence set forth in SEQ ID NO:1.

17. The method of claim 3, wherein the fragment comprises nt 1 to nt 1334, nt 1 to nt 1294, nt 1 to nt 1206, nt 1 to nt 910, nt 450 to nt 1167, nt 450 to nt 1425, nt 115 to nt 910, nt 231 to nt 910, nt 450 to nt 910, nt 579 to nt 910, nt 1 to nt 800, nt 450 to 800, nt 115 to nt 800, nt 231 to nt 800, or nt 450 to nt 800 of SEQ ID NO:1.

18. The method of claim 4, wherein the gene product is a protein.

19. The method of claim 5, wherein the cell is a hamster cell and/or an ovarian cell.

20. The method of claim 19, wherein the cell is a CHO cell.

21. A method of recombinantly expressing a protein gene product comprising:

expressing in a cell a gene product from an expression cassette comprising a coding sequence under the control of a nucleic acid sequence that comprises SEQ ID NO: 2, wherein the expression is induced by modifying the temperature of the cell.

* * * * *

SEQUENCE LISTING

<160> NUMBER OF SEQ ID NOS: 46

<210> SEQ ID NO 1
<211> LENGTH: 1505
<212> TYPE: DNA
<213> ORGANISM: Cricetulus griseus

<400> SEQUENCE: 1
gcatgctggc tgggctgggc tccattgtgt gcacattaat ttgtaagctg ctctaaagat    60
gaacttccag gcagtgagct ggaagaagcg agttagacag aaatttattg ttggtggggg   120

-continued

| | |
|---|---|
| atggtgtctg aaatccttta gactgtgtcc ctccccctttt tttgagacag ggttttatat | 180 |
| agcccaggtt ggctcagaat tctgcctcgt gggatcaacc tactgagcta tatcccaag | 240 |
| tcttaaacta gtgaggtcaa accaccctat cagaggggtt gcctaagatc atcggaaaac | 300 |
| acaagtattt acactgagat tcataacagt agcaaaatta cggtgtgaag cagcagtgaa | 360 |
| ataaatttta tgattggggg acaccacaac atgagaatct gtgtccaagg gtcatagaat | 420 |
| taggaaggtt gagaactatt agccaatcta gtagaccact agggcttcc cctccttccc | 480 |
| tggagctgac cttgccacca gagggcgaca gcatcagtga ggttcccact ccccctcaca | 540 |
| ttgatgctga ctttagggac acattgtgct ctgtctggca gatggcccag cacacatgcc | 600 |
| ggagtcacga gtcacgtgcc ataagggcaa actgaagtat ggaaattagg gaaaactcga | 660 |
| tgtctctggt ttgtgctggt ctcccagacc agggtcacta ggctccctca tgccactccc | 720 |
| aatccgggac agtcctggca gcagaggcgt ggaaaactga ggggttgtt gggtgtgtt | 780 |
| ttgctagcct caggcgccgg gtggggctcg gggcgggccg gcactccttg gcgggcctc | 840 |
| ccggatgcta gccgctataa ggccagccgg actgcgacac agtccatccc ctcgaccact | 900 |
| cctttggctc ttcgctgtct acctgcctac ggtgcggtga gctcttgctg gggcagttct | 960 |
| aggtccctct aaggtcggct cctgggctgg ggggtcaagc cacttcctgc cacatccagc | 1020 |
| ccctacgggt tccgcgggtg gtctacactg gggtctaaat ctgccgagca cggggtggtg | 1080 |
| gggtgggg tggggtggg gtgggaggt aagaggggga ggtagggaga gccaaggttc | 1140 |
| agcttggttg tgccaggcaa gcccggaggc taaggcatcc ttatagggcg gctccccgag | 1200 |
| tctgctttc tggggtgcag gagggttcgc cctgggtgtg tcattgtcgt cgcagtgtgt | 1260 |
| ggtcctgtca ggaagtgccc tggagcagcc tccatctctt cctctgctca gtcatattcc | 1320 |
| ccagctctct tggaatccct ggagatcagt gttcagacac cccaaagccg cttccgttct | 1380 |
| tacatccctg accctagttg ccctgggctg cctgcacctg tgttggctaa ggctagctgg | 1440 |
| ttcagacagg cagcactgac tagcccctct ctgtcaaaca gcttcttcta gcccagtggt | 1500 |
| caatt | 1505 |

<210> SEQ ID NO 2
<211> LENGTH: 1505
<212> TYPE: DNA
<213> ORGANISM: Mus musculus

<400> SEQUENCE: 2

| | |
|---|---|
| tcaaaacttt tcacttgaga tgagtaactg agaatgctcg ctgggcttgg ctctactatg | 60 |
| tgcacattca tgcataagct gctctaagga tgaaaatcca ggcagtgagt gggaggaggc | 120 |
| gagtgatgtt gctagaaatt tatggttggt gggggatgct gtttaaaatc ttttagactg | 180 |
| tgttctttcc ccatgccccc tttgatacaa ggctcaaaat tctacctttt gggatcaacg | 240 |
| tctttagcta tatatcaaga tttagaccag tggttctcaa cctgtgggtt gagaccct | 300 |
| tcacaggaat tgcctaagac catctgaaaa cacagatata cacattaaga ttcataacag | 360 |
| tagcaaaatt atagctatga agtagaaacg agaataactt tatgattggg ggaccaccac | 420 |
| aacttgaaga acagtattaa agggccgcag cattagtcag gttgagtgag aaccatttct | 480 |
| tagaggatgt ggtagacaga ctgcttcccc tccctcactt ggggaccttg ccactagagg | 540 |
| gcaacagcat cagtgtggtt cccagtcccc ctcacactga tgctaacttt aaggacactg | 600 |
| ctctcgggct ggcagaaggt tcagcacaca agccagagtt tcgagtcacg tgccagaagg | 660 |
| gaaaactaaa cacggaatta gagaaaactt gatgcctctg gcttgcactg gtctcctttg | 720 |

```
ggcccgttag ggcccgctaa actccctcat tccgctccta atcctggaca gtccaggcaa      780
caggggcgtg gaaagttgag ggggctggga tgttcgtttg ccttgcctca ggcgctgggt      840
ggggtcgggg cgtgccagca ctccctgggc ggacctcacg gatgctggcc actataaggc      900
cggccagact gcgacacatt ccatcccctc gaccactcct ttggcgcttc gctgtcgacc      960
gtgcggtgag ctctcgctgg ggggtccctc tagggtcttt ctgctcctgg caagggggtt     1020
aagccacttc cttcccccgt cagcctctgc aggctcagtg ggtggaatgc attgggatcc     1080
aagttttcgg agcccaggga ggcagggaga gccatgatta ggtgggttgt atcaggcaaa     1140
cccagaggct aatgcatccc tatggggcgg caacctgagt ctgctcttct ggggtgcagg     1200
agggtttgcc ctgggtgtgt catcgtccca gtgtgtggct atgtcaggag gtgcccaggg     1260
gcactctcca ttctcttcct tgctcagtca tatgccctag ttctcttgga agccctggag     1320
gacagtgctc acagatccca aagccccttc cattcttata tccctcacct aagttgcccc     1380
ggctgccacc tgtgttggct tgagactgac tgcctcaggc agggggtgg tgagagaact      1440 ctctgctatc agcagcactg actagcccct ctgtcaaaca gcttcttcta gcccagtgat     1500
cagtc                                                                 1505

<210> SEQ ID NO 3
<211> LENGTH: 1505
<212> TYPE: DNA
<213> ORGANISM: Rattus norvegicus

<400> SEQUENCE: 3
tgaaaacttt ttacttgaga tgagtaagta actaacgatg cttcctgggc ttggctccac       60
tgtgtgcaca ttaaggcata agctgctctg aggatgaaat tccaggcagt gagtgggagg      120
aggcaagtga tgttgttaga aatttatggt tggtggggga tgctgtttaa aatcttttag      180
actgtgttcc ccttctgtct cccttttgag acatgggtct tatataggtt ggctcaaaat      240
tctacctctt gggatcagcc tatctcatca agatttagcc cagtggtgct caacctgtgg      300 agacccettt cacaggaatt gcctgagacc atctgaaaac acagtattta tgtcacgatt      360
cataacagta gcaaaaatat agttatgaag cagcaacgaa aatcacttta tggttggagc      420
gtcaccacaa catgaagaat gtattaatcc gcagtattag agaggtcgag aaccactatc      480
ttagaggatg cggtagactg actgcttccc ctctcgcttg gagttgacct tgccactaga      540 ggcaacagc atcagtattg ttcccagtcc ccctcacact gattcgaact ttaaggacac       600
tgatctctgg ctggtagagg gttcagcaca cataccagag ttacgagtca cgtgccagaa      660
gggcaaactg aacacggaat tagagggaac tcgatgtctc cggcttgcac tggtcttctc      720
ttgcactaga atccttcatc ctgctcccag tccgggacgt ccaggcaaca agggcgtgga      780
aagtgagggg gctggaggt gtgtttgcct tgcctcaggc gctgggtggg gttgggcgt        840 gccagcactc cctgggcggg cctcaccgat gctggccact ataaggccag ccagactgcg      900
acacagtcca tcccctcgac cactcttttg gcgcttcatt gtcgacgtgt ggtgagctct      960
cactggggcg tccctctaag atctgtccac tcctggtcta ggggttaagc ctttcctgcc     1020
ctagtcagcc tctgcgggct ccatgggtgg aatgcactgg gatccaagtt tcggagccc      1080 agggaagcag ggagagccat ggtctgctgg gctgtaccag acaaaccccg aggctaaggc     1140
atccccatgg gcggcaacct gaatctgctt ttctggggtg caggagggtt tgccctgggt     1200
gtgtcatcct cgtcccagtg tgtggccctg tcaggaggtt ccaggggca gcctccattc      1260
```

```
tcttccttgc tcagtcatat gctccagttc tcttggaagc cctggaggac agtgttcaca    1320
gaccccaaag ccccttccat tcttagactc ctcacctcag tggccctggc tgctacctgt    1380
gttggcttga ggctagctgc ttcaggcagg tagtctcctg gctcagggga tggtgagagg    1440
actctctgct accagtagca ctgaatagcc cctctgtcaa acagcttcta gcccagtggt    1500
cagtc                                                                1505

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
atggcatgcc ccctggatca g                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
cattgtagat caaagccaag g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
atggcatgcc ccctggatca g                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
gccaatggtg agctccttct g                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
ctcctttggc tcttcgctgt c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
```

-continued atggcatgcc ccctggatca g    21

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ccttcttgtg gccatcttcc    20

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
ctgagattgc aaggctgatg g    21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
gccaatggtg agctccttct g    21

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
cattgtagat caaagccaag g    21

<210> SEQ ID NO 14
<211> LENGTH: 32
<212> TYPE: DNA
<213> ORGANISM: Artificial Sequence
<220> FEATURE:
<223> OTHER INFORMATION: Synthetic primer

<400> SEQUENCE: 14
gatgatggta ccggaagaag cgagttagac ag    32

<210> SEQ ID NO 15
<211> LENGTH: 32
<212> TYPE: DNA
<213> ORGANISM: Artificial Sequence
<220> FEATURE:
<223> OTHER INFORMATION: Synthetic primer

<400> SEQUENCE: 15
gatgataagc ttagacccca gtgtagacca cc    32

<210> SEQ ID NO 16
<211> LENGTH: 31
<212> TYPE: DNA

```
<213> ORGANISM: Artificial Sequence
<220> FEATURE:
<223> OTHER INFORMATION: Synthetic primer

<400> SEQUENCE: 16
gatgatggta ccgcatgctg gctgggctgg g                                 31

<210> SEQ ID NO 17
<211> LENGTH: 34
<212> TYPE: DNA
<213> ORGANISM: Artificial Sequence
<220> FEATURE:
<223> OTHER INFORMATION: Synthetic primer

<400> SEQUENCE: 17
gatgatggta cctgagacag ggttttatat agcc                              34

<210> SEQ ID NO 18
<211> LENGTH: 34
<212> TYPE: DNA
<213> ORGANISM: Artificial Sequence
<220> FEATURE:
<223> OTHER INFORMATION: Synthetic primer

<400> SEQUENCE: 18
gatgatggta ccggatcaac ctactgagct atat                              34

<210> SEQ ID NO 19
<211> LENGTH: 35
<212> TYPE: DNA
<213> ORGANISM: Artificial Sequence
<220> FEATURE:
<223> OTHER INFORMATION: Synthetic primer

<400> SEQUENCE: 19
gatgatggta cccacaagta tttacactga gattc                             35

<210> SEQ ID NO 20
<211> LENGTH: 32
<212> TYPE: DNA
<213> ORGANISM: Artificial Sequence
<220> FEATURE:
<223> OTHER INFORMATION: Synthetic primer

<400> SEQUENCE: 20
gatgatggta ccatgccgga gtcacgagtc ac                                32

<210> SEQ ID NO 21
<211> LENGTH: 32
<212> TYPE: DNA
<213> ORGANISM: Artificial Sequence
<220> FEATURE:
<223> OTHER INFORMATION: Synthetic primer

<400> SEQUENCE: 21
gatgatggta ccagaggcgt ggaaaactga gg                                32

<210> SEQ ID NO 22
<211> LENGTH: 30
<212> TYPE: DNA
<213> ORGANISM: Artificial Sequence
<220> FEATURE:
<223> OTHER INFORMATION: Synthetic primer

<400> SEQUENCE: 22
gatgatggta ccactccttg ggcgggcctc                                   30
```

<210> SEQ ID NO 23
<211> LENGTH: 32
<212> TYPE: DNA
<213> ORGANISM: Artificial Sequence
<220> FEATURE:
<223> OTHER INFORMATION: Synthetic primer

<400> SEQUENCE: 23
gatgatggta ccggatgcta gccgctataa gg                     32

<210> SEQ ID NO 24
<211> LENGTH: 31
<212> TYPE: DNA
<213> ORGANISM: Artificial Sequence
<220> FEATURE:
<223> OTHER INFORMATION: Synthetic primer

<400> SEQUENCE: 24
gatgatggta ccaggtcggc tcctgggctg g                      31

<210> SEQ ID NO 25
<211> LENGTH: 30
<212> TYPE: DNA
<213> ORGANISM: Artificial Sequence
<220> FEATURE:
<223> OTHER INFORMATION: Synthetic primer

<400> SEQUENCE: 25
gatgatggta cctagggcgg ctccccgagt                        30

<210> SEQ ID NO 26
<211> LENGTH: 32
<212> TYPE: DNA
<213> ORGANISM: Artificial Sequence
<220> FEATURE:
<223> OTHER INFORMATION: Synthetic primer

<400> SEQUENCE: 26
gatgatggta cctcgcagtg tgtggtcctg tc                     32

<210> SEQ ID NO 27
<211> LENGTH: 33
<212> TYPE: DNA
<213> ORGANISM: Artificial Sequence
<220> FEATURE:
<223> OTHER INFORMATION: Synthetic primer

<400> SEQUENCE: 27
gatgataagc ttaattgacc actgggctag aag                    33

<210> SEQ ID NO 28
<211> LENGTH: 34
<212> TYPE: DNA
<213> ORGANISM: Artificial Sequence
<220> FEATURE:
<223> OTHER INFORMATION: Synthetic primer

<400> SEQUENCE: 28
gatgataagc tttcagggat gtaagaacgg aagc                   34

<210> SEQ ID NO 29
<211> LENGTH: 33
<212> TYPE: DNA
<213> ORGANISM: Artificial Sequence
<220> FEATURE:

<223> OTHER INFORMATION: Synthetic primer

<400> SEQUENCE: 29
gatgataagc ttcttcctga caggaccaca cac                               33

<210> SEQ ID NO 30
<211> LENGTH: 33
<212> TYPE: DNA
<213> ORGANISM: Artificial Sequence
<220> FEATURE:
<223> OTHER INFORMATION: Synthetic primer

<400> SEQUENCE: 30
gatgataagc ttgcttgcct ggcacaacca agc                               33

<210> SEQ ID NO 31
<211> LENGTH: 32
<212> TYPE: DNA
<213> ORGANISM: Artificial Sequence
<220> FEATURE:
<223> OTHER INFORMATION: Synthetic primer

<400> SEQUENCE: 31
gatgataagc tttagaccac ccgcggaacc cg                                32

<210> SEQ ID NO 32
<211> LENGTH: 33
<212> TYPE: DNA
<213> ORGANISM: Artificial Sequence
<220> FEATURE:
<223> OTHER INFORMATION: Synthetic primer

<400> SEQUENCE: 32
gatgataagc ttggcaggta gacagcgaag agc                               33

<210> SEQ ID NO 33
<211> LENGTH: 31
<212> TYPE: DNA
<213> ORGANISM: Artificial Sequence
<220> FEATURE:
<223> OTHER INFORMATION: Synthetic primer

<400> SEQUENCE: 33
gatgataagc ttgcggctag catccgggag g                                 31

<210> SEQ ID NO 34
<211> LENGTH: 32
<212> TYPE: DNA
<213> ORGANISM: Artificial Sequence
<220> FEATURE:
<223> OTHER INFORMATION: Synthetic primer

<400> SEQUENCE: 34
gatgatggta ccatgccgga gtcacgagtc ac                                32

<210> SEQ ID NO 35
<211> LENGTH: 32
<212> TYPE: DNA
<213> ORGANISM: Artificial Sequence
<220> FEATURE:
<223> OTHER INFORMATION: Synthetic primer

<400> SEQUENCE: 35
gatgataagc ttatgccgga gtcacgagtc ac                                32

<210> SEQ ID NO 36
<211> LENGTH: 33
<212> TYPE: DNA
<213> ORGANISM: Artificial Sequence
<220> FEATURE:
<223> OTHER INFORMATION: Synthetic primer

<400> SEQUENCE: 36
gatgatggta ccggcaggta gacagcgaag agc                              33

<210> SEQ ID NO 37
<211> LENGTH: 32
<212> TYPE: DNA
<213> ORGANISM: Artificial Sequence
<220> FEATURE:
<223> OTHER INFORMATION: Synthetic primer

<400> SEQUENCE: 37
gatgatggta cccctcatgc cactcccaat cc                               32

<210> SEQ ID NO 38
<211> LENGTH: 32
<212> TYPE: DNA
<213> ORGANISM: Artificial Sequence
<220> FEATURE:
<223> OTHER INFORMATION: Synthetic primer

<400> SEQUENCE: 38
gatgataagc ttcctcatgc cactcccaat cc                               32

<210> SEQ ID NO 39
<211> LENGTH: 32
<212> TYPE: DNA
<213> ORGANISM: Artificial Sequence
<220> FEATURE:
<223> OTHER INFORMATION: Synthetic primer

<400> SEQUENCE: 39
gatgatctcg agactcccaa tccgggacag tc                               32

<210> SEQ ID NO 40
<211> LENGTH: 33
<212> TYPE: DNA
<213> ORGANISM: Artificial Sequence
<220> FEATURE:
<223> OTHER INFORMATION: Synthetic primer

<400> SEQUENCE: 40
gatgatctcg agcagcgaag agccaaagga gtg                              33

<210> SEQ ID NO 41
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 41
tggacagtcc                                                        10

<210> SEQ ID NO 42
<211> LENGTH: 10
<212> TYPE: DNA
<213> ORGANISM: Artificial Sequence
<220> FEATURE:
<223> OTHER INFORMATION: Synthetic oligonucleotide

```
<400> SEQUENCE: 42
gggacagtcc                                                              10

<210> SEQ ID NO 43
<211> LENGTH: 178
<212> TYPE: DNA
<213> ORGANISM: Mus musculus

<400> SEQUENCE: 43
cctcattccg ctcctaatcc tggacagtcc aggcaacagg ggcgtggaaa gttgaggggg       60
ctgggatgtt cgtttgcctt gcctcaggcg ctgggtgggg tcggggcgtg ccagcactcc      120
ctgggcggac ctcacggatg ctggccacta taaggccggc cagactgcga cacattcc       178

<210> SEQ ID NO 44
<211> LENGTH: 176
<212> TYPE: DNA
<213> ORGANISM: Rattus norvegicus

<400> SEQUENCE: 44
cttcatcctg ctcccagtcc gggacgtcca ggcaacaagg gcgtggaaag tgagggggct       60
gggaggtgtg tttgccttgc ctcaggcgct gggtgggggtt ggggcgtgcc agcactccct     120
gggcgggcct caccgatgct ggccactata aggccagcca gactgcgaca cagtcc          176

<210> SEQ ID NO 45
<211> LENGTH: 180
<212> TYPE: DNA
<213> ORGANISM: Cricetulus griseus

<400> SEQUENCE: 45
cctcatgcca ctcccaatcc gggacagtcc tggcagcaga ggcgtggaaa actgaggggg       60
ttgttggggt gtgttttgct agcctcaggc gccgggtggg gctcggggcg ggccggcact     120
ccttgggcgg gcctcccgga tgctagccgc tataaggcca gccggactgc gacacagtcc     180

<210> SEQ ID NO 46
<211> LENGTH: 32
<212> TYPE: DNA
<213> ORGANISM: Artificial Sequence
<220> FEATURE:
<223> OTHER INFORMATION: Synthetic primer

<400> SEQUENCE: 46
gatgatggta cctacggtgt gaagcagcag tg                                     32
```